United States Patent [19]
Hediger et al.

[11] Patent Number: 5,739,284
[45] Date of Patent: Apr. 14, 1998

[54] COMPOSITIONS CORRESPONDING TO A HIGH-AFFINITY GLUTAMATE TRANSPORTER MOLECULE AND METHODS FOR MAKING AND USING SAME

[75] Inventors: Matthias Hediger, Wellesley, Mass.; Yoshikatsu Kanai, Tokyo, Japan

[73] Assignee: Brigham and Women's Hospital, Inc., Boston, Mass.

[21] Appl. No.: 529,654

[22] Filed: Sep. 18, 1995

Related U.S. Application Data

[63] Continuation of Ser. No. 194,719, Feb. 10, 1994, abandoned, which is a continuation-in-part of Ser. No. 965,676, Oct. 19, 1992, abandoned.

[51] Int. Cl.$^6$ .................. C07K 14/47; C07K 14/705; C12N 15/12
[52] U.S. Cl. .................. 530/350; 530/395; 536/23.1; 536/23.5
[58] Field of Search ................... 530/350, 395; 536/23.1, 23.5

[56] References Cited

PUBLICATIONS

D. Nicholls et al. Trends in Phamacol. Sci. 11:462–468 (1990).
R.D. Blakely et al. Proc. Natl. Acad. Sci 85:9846–9850 (Dec. 1988).
M.A. Hediger et al. Nature 330:379–381 (Nov. 1987).
N.C. Danbolt et al. Neuroscience 51(2) 295–310 (1992).
N.C. Danbolt et al. Biochemistry 29:6734–6740 (1990).
B.I. Kamner et al. FEBS Letts. 94(2) 245–248 (1978).

*Primary Examiner*—Rebecca E. Prouty
*Attorney, Agent, or Firm*—Cesari and McKenna, LLP

[57] ABSTRACT

The present invention features an excitatory amino acid carrier protein which has high affinity for glutamate and is associated with neuronal glutamate transport, and methods of making and using the protein.

6 Claims, 13 Drawing Sheets

```
GCGCACGGCC GAGCCAGCG CACAATAGCG GCGACAGCC ATG GGG AAA CCG GCG       54
                                          Met Gly Lys Pro Ala
                                           1                5

AGG AAA GGA TGC GAG TGG AAG CGC TTC CTG AAG AAT AAC TGG GTG TTG   102
Arg Lys Gly Cys Glu Trp Lys Arg Phe Leu Lys Asn Asn Trp Val Leu
             10              15              20

CTG TCC ACC GTG GCC GCG GTG GTG CTA GGC ATT ACC ACA GGA GTC TTG   150
Leu Ser Thr Val Ala Ala Val Val Leu Gly Ile Thr Thr Gly Val Leu
         25              30              35

GTT CGA GAA CAC AGC AAC CTC TCA ACT CTA GAG AAA TTC TAC TTT GCT   198
Val Arg Glu His Ser Asn Leu Ser Thr Leu Glu Lys Phe Tyr Phe Ala
         40              45              50

TTT CCT GGA GAA ATT CTA ATG CGG ATG CTG AAA CTC ATC ATT TTG CCA   246
Phe Pro Gly Glu Ile Leu Met Arg Met Leu Lys Leu Ile Ile Leu Pro
     55              60              65

TTA ATT ATA TCC AGC ATG ATT ACA GGT GTT GCT GCA CTG GAT TCC AAC   294
Leu Ile Ile Ser Ser Met Ile Thr Gly Val Ala Ala Leu Asp Ser Asn
70           75              80              85

GTA TCC GGA AAA ATT GGT CTG CGC GCT GTG CTG TAT TAT TTC TGT ACC   342
Val Ser Gly Lys Ile Gly Leu Arg Ala Val Leu Tyr Tyr Phe Cys Thr
             90              95             100

ACT CTC ATT GCT GTT ATT CTA GGT ATT GTG CTG GTG GTG AGC ATC AAG   390
Thr Leu Ile Ala Val Ile Leu Gly Ile Val Leu Val Val Ser Ile Lys
             105             110             115

CCT GGT GTC ACC CAG AAA GTG GGT GAA ATT GCG AGG ACA GGC AGC ACC   438
Pro Gly Val Thr Gln Lys Val Gly Glu Ile Ala Arg Thr Gly Ser Thr
         120             125             130

CCT GAA GTC AGT ACG GTG GAT GCC ATG TTA GAT CTC ATC AGG AAT ATG   486
Pro Glu Val Ser Thr Val Asp Ala Met Leu Asp Leu Ile Arg Asn Met
     135             140             145

TTC CCT GAG AAT CTT GTC CAG GCC TGT TTT CAG CAG TAC AAA ACT AAG   534
Phe Pro Glu Asn Leu Val Gln Ala Cys Phe Gln Gln Tyr Lys Thr Lys
150             155             160             165

CGT GAA GAA GTG AAC CCT GCC AGT GAT CCA GAG ATG AAC ATG ACA GAA   582
Arg Glu Glu Val Asn Pro Ala Ser Asp Pro Glu Met Asn Met Thr Glu
             170             175             180
```

FIG. 1A

```
GAG TCC TTC ACA GCT GTC ATG ACA ACT GCA ATT TCC AAG AAC AAA ACA   630
Glu Ser Phe Thr Ala Val Met Thr Thr Ala Ile Ser Lys Asn Lys Thr
            185                 190                 195

AAG GAA TAC AAA ATT GTT GGC ATG TAT TCA GAT GGC ATA AAC GTC CTG   678
Lys Glu Tyr Lys Ile Val Gly Met Tyr Ser Asp Gly Ile Asn Val Leu
        200                 205                 210

GGC TTG ATT GTC TTT TGC CTT GTC TTT GGA CTT GTC ATT GGA AAA ATG   726
Gly Leu Ile Val Phe Cys Leu Val Phe Gly Leu Val Ile Gly Lys Met
    215                 220                 225

GGA GAA AAG GGA CAA ATT CTG GTG GAT TTC TTC AAT GCT TTG AGT GAT   774
Gly Glu Lys Gly Gln Ile Leu Val Asp Phe Phe Asn Ala Leu Ser Asp
230                 235                 240                 245

GCA ACC ATG AAA ATC GTT CAG ATC ATC ATG TGT TAT ATG CCA CAT GGT   822
Ala Thr Met Lys Ile Val Gln Ile Ile Met Cys Tyr Met Pro His Gly
                250                 255                 260

ATT TTG TTC CTG ATT GCT GGG AAG ATC ATA GAA GTT GAA GAC TGG GAA   870
Ile Leu Phe Leu Ile Ala Gly Lys Ile Ile Glu Val Glu Asp Trp Glu
            265                 270                 275

ATA TTC CGC AAG CTG GGC CTT TAC ATG GCC ACA GTC CTG ACT GGG CTT   918
Ile Phe Arg Lys Leu Gly Leu Tyr Met Ala Thr Val Leu Thr Gly Leu
        280                 285                 290

GCA ATC CAC TCC ATT GTA ATT CTC CCG CTG ATA TAT TTC ATA GTC GTA   966
Ala Ile His Ser Ile Val Ile Leu Pro Leu Ile Tyr Phe Ile Val Val
    295                 300                 305

CGA AAG AAC CCT TTC CGA TTT GCC ATG GGA ATG GCC CAG GCT CTC CTG  1014
Arg Lys Asn Pro Phe Arg Phe Ala Met Gly Met Ala Gln Ala Leu Leu
310                 315                 320                 325

ACA GCT CTC ATG ATC TCT TCC AGT TCA GCA ACA CTG CCT GTC ACC TTC  1062
Thr Ala Leu Met Ile Ser Ser Ser Ser Ala Thr Leu Pro Val Thr Phe
                330                 335                 340

CGC TGT GCT GAA GAA AAT AAC CAG GTG GAC AAG AGG ATC ACT CGA TTC  1110
Arg Cys Ala Glu Glu Asn Asn Gln Val Asp Lys Arg Ile Thr Arg Phe
            345                 350                 355

GTG TTA CCC GTT GGT GCA ACA ATC AAC ATG GAT GGG ACT GCG CTC TAT  1158
Val Leu Pro Val Gly Ala Thr Ile Asn Met Asp Gly Thr Ala Leu Tyr
        360                 365                 370

GAA GCA GTG GCA GCG GTG TTT ATT GCA CAG TTG AAT GAC CTG GAC TTG  1206
Glu Ala Val Ala Ala Val Phe Ile Ala Gln Leu Asn Asp Leu Asp Leu
    375                 380                 385
```

FIG. 1B

```
GGC ATT GGG CAG ATC ATC ACC ATC AGT ATC ACG GCC ACA TCT GCC AGC    1254
Gly Ile Gly Gln Ile Ile Thr Ile Ser Ile Thr Ala Thr Ser Ala Ser
390                     395                 400                 405

ATC GGA GCT GCT GGC GTG CCC CAG GCT GGC CTG GTG ACC ATG GTG ATT    1302
Ile Gly Ala Ala Gly Val Pro Gln Ala Gly Leu Val Thr Met Val Ile
                    410                 415                 420

GTG CTG AGT GCC GTG GGC CTG CCC GCC GAG GAT GTC ACC CTG ATC ATT    1350
Val Leu Ser Ala Val Gly Leu Pro Ala Glu Asp Val Thr Leu Ile Ile
            425                 430                 435

GCT GTC GAC TGG CTC CTG GAC CGG TTC AGG ACC ATG GTC AAC GTC CTT    1398
Ala Val Asp Trp Leu Leu Asp Arg Phe Arg Thr Met Val Asn Val Leu
        440                 445                 450

GGT GAT GCT TTT GGG ACG GGC ATT GTG GAA AAG CTC TCC AAG AAG GAG    1446
Gly Asp Ala Phe Gly Thr Gly Ile Val Glu Lys Leu Ser Lys Lys Glu
455                 460                 465

CTG GAG CAG ATG GAT GTT TCA TCT GAA GTC AAC ATT GTG AAT CCC TTT    1494
Leu Glu Gln Met Asp Val Ser Ser Glu Val Asn Ile Val Asn Pro Phe
470                 475                 480                 485

GCC TTG GAA TCC ACA ATC CTT GAC AAC GAA GAC TCA GAC ACC AAG AAG    1542
Ala Leu Glu Ser Thr Ile Leu Asp Asn Glu Asp Ser Asp Thr Lys Lys
                490                 495                 500

TCT TAT GTC AAT GGA GGC TTT GCA GTA GAC AAG TCT GAC ACC ATC TCA    1590
Ser Tyr Val Asn Gly Gly Phe Ala Val Asp Lys Ser Asp Thr Ile Ser
            505                 510                 515

TTC ACC CAG ACC TCA CAG TTC TAGGGCCCT                               1620
Phe Thr Gln Thr Ser Gln Phe
        520             525
```

FIG. 1C

```
AGGCGGCGGT GACAGCGGCA TCGGCAGGGC CAGCGCGCAC TCTCTCCCAG GCGCACCGGC 60
GTCTTGCTTC CTCCGCGCCG CCCAGCTGAC GGCCATCCCC GGCCGAGGCG CGCACAGCCC 120
AGCCCCGCAC ACAACAGCGG CGACCGCGGG GCCCGCTCGG AGCCCGGACG GCCGCCATGG 180
GGAAGCCGGC GAGGAAAGGA TGCGACAGCA AGCGCTTCCT GAAGAATAAC TGGCTGCTGC 240
TCTCCACCGT GGTCGCGGTG GTGCTAGGCA TTGTCATAGG AGTCTTGGTT CGAGAATACA 300
GCAATCTCTC AACTCTGGAT AAATTCTACT TTGCTTTTCC TGGAGAAATC CTGATGAGGA 360
TGCTGAAACT CGTCATTCTG CCATTAATTG TATCCAGCAT GATTACAGGT GTTGCTGCAC 420
TGGATTCCAA TGTTTCTGGG AAAATTGGTC TGCGTGCTGT CTTGTATTAT TTCTGCACCA 480
CTATCATTGC TGTAATTCTA GGTATTGTGT TGGTGGTGAG CATCAAGCCT GGGGTCACCC 540
AGAAAGTGGA TGAAATCGAC AGGACAGGCA GCACCCCTGA AGTCAGCACA GTGGATGCC 600
TGTTAGACCT GATCAGGAAT ATGTTCCCTG AGAACCTCGT GCAGGCCTGT TTTCAGCAG 660
ACAAAACCAC TCGTGAAGAA GTGACAGCTT CCGATGATAC GGGAAGAAT GGGACTGAAG 720
AGTCTGTCAC AGCCGTCATG ACAACAGCCG TGTCTGAGAA CAGAACAAAG GAGTACAGAG 780
TCGTGGGCCT GTATTCAGAT GGCATCAATG TCCTGGGCTT GATTGTCTTC TGCCTCGTGT 840
TCGGACTCGT CATCGGGAAA ATGGGAGAAA AGGGACAGAT TCTGGTGGAT TTCTTCAATG 900
CTTTGAGTGA CGCAACCATG AAAATCGTTC AGATCATTAT GTGTTACATG CCGCTTGGTA 960
TTTTGTTCCT GATTGCCGGG AAGATCATAG AAGTTGAAGA CTGGGAAATT TTCCGCAAGC 1020
TGGGCTTGTA CATGGTCACC GTCCTGAGTG GCTTGCAAT CCACTCCATT GTCATTCTCC 1080
CACTGATATA TTTCATTGTG GTGCGAAAGA ACCCTTTCCG ATTTGCCATG GGAATGACCC 1140
```

FIG. 2A

```
AGGCTCTCCT GACAGCACTC ATGATCTCTT CCAGTTCAGC AACACTGCCT GTCACCTTCC    1200
GCTGTGCAGA AGAAAAGAAC CGTGTGGACA AGAGGATCAC TCGATTTGTG TTGCCCGTTG    1260
GTGCCACAAT CAACATGGAT GGGACCGCAC TCTATGAGGC AGTGGCAGCA GTGTTTATTG    1320
CACAGTTGAA TGATATGGAC TTGAGCATTG GCAGATCAT CACTATCAGC GTCACAGCTA     1380
CAGCTGCCAG CATTGGAGCT GCCGGTGTGC CCAGGCTGG CCTGGTGACC ATGGTGATTG     1440
TGCTGAGTGC TGTGGGGCTG CCCGCTGAGG ATGTCACCCT GATCATTGCT GTCGACTGGC   1500
TCCTGGACCG GTTCAGGACT GTGGTCAACG TCCTTGGTGA TGCTTTTGGA ACCGGCATTG    1560
TGGAAAAGCT CTCCAAGAAG GAGTTGGAGC AGATGGATG  TTCATCTGAA GTCAACATCG   1620
TGAACCCTTT TGCCTTGGAA TCTGCAACCC TCGACAACGA AGACTCAGAC ACCAAGAAGT    1680
CCTACATCAA CGGAGGATTT GCAGTAGACA AGTCTGACAC AATCTCTTTC ACCCAGACCT    1740
CACAGTTCTA GAGGCACTGG CTTCACAGGA CTGTCATGAA GGACCTTCCA TGAGAGTCAT    1800
CTCTTAGCAA ATGCAAACAT TAATTAAGGA AAATGCAAAT GGCCACTGTA CATTTAATTT    1860
GATATACAGA CGTCCAGATT ATTTTCTATA TTCAAATTCT GAGCCTTTGC TCTCTGGGTT    1920
TTGGGATTTG GGCAGGGTG GGGTAACATG AAAGGAAATT CTTGAAAGTT GTATTATCTG     1980
AATTTTTTAA AATTCCATAG GCCAAAGTTT AGAAGTATGC AAACTAACTT GGAATTAGAT    2040
AATGGGTAG  GAAGAGAAAT TGCTTTTTCA TGTACAGACT AGTATTTTTT AAAAAATAAT    2100
TCTGTCATTG GTTACAAATT TTTACTCAGG CTTTCTATTG GCATGGATTT CCTTTGACCT    2160
CACTTTTTTA TAGATTATTC TTCATCTAAC CTTCCCCACT AATGTGCCAA ATTGTCCATA    2220
CTGAACTCCT TTCTAGCCAA TTTCAAAGAA ATTGCTTTGA AAGAAAACAA ACCAGCACAG    2280
TTCCTCAATA ACAGTCTTAA GATGGGTATA GGCTTTGGGG AGGGAAGGAG ACGAGTTCTT    2340
TTACTAATGT ACTGTATTGG GATGCTGATA ACTGTTAACC CAGTGTTCAC TATAGAGCTA    2400
TATATATATA TATGTATGTA TGTGTATGTA TATATTTATT ATTTTCATAT AATTCGCCAG    2460
AGATCAGAAT TGAACTGTCA ATGTGAAATA AAGAGCTGTC CTTGTACTTG AATAGTTATT    2520
ACAATTCCAA CCCAGATCTG CTGTGGGGCT TATCAGAACT CTTTTCCTTT TTATCAGAAT    2580
TAGAGAAATC ATGTTGTCGG ATCACTTAAG GTCTGTGTAT CAGCCCCAAG CAGAGATGTA    2640
```

FIG. 2B

```
TTGTGGTGAC AGTCCAGGCT GGCCATTCAC TTACATCTCC CAGATTGGTG CTGCCTGGAG 2700
TGAACCCATA TCAGCTGTAC ATAAGACTGC ACACAAAGGT GCCACTCATG AAAGGCTGGA 2760
CGTGCTTTTA TCTAATTAGA AGGCCTCCTT CTCCTGTGTG GACTCATGCC AGGTAGAGAA 2820
ACATTTTGCT GGCCTTGCAC TTTTGTATCC ATCAGCACCC AAACAACAGT GGCAGATGAC 2880
CAGCTACGTT GCATTTGAAT ATAGAATCCA CGGTTTGAAC AAGCCACACT GCAGAAAAAG 2940
AGCTGTGTCA ACCCTGGGTT CTTGCAGAGT AAACCACGGG ACCTGAGACG CTGGTGCCAG 3000
CAGGTGAGGA GTGAGTCTTC CATTCTGCAA CGCTTGTCTC CTCCTCTAAC GATGGCTTCA 3060
CTGTTAATCT TGGCCCTGTT CATTAAAATC CTTTGCTTGT CATCCTCCTG CTAATTTATG 3120
AAGATAACTG ATAAAAGTCT GTGCTTCAGT TCTCATCTTG TAAATAATGC TTAACATGTA 3180
CTTACACTGG CATCCAAAAC AGTAATGCAG TCTTATGTAG CCAGCTCAAA CATGTGCTTT 3240
TAAAATTAAG CCAGAAATTG TGCCAAAGAA AGCAGGGAAG TAAATACTCA GTATTGACCA 3300
TCTGCACTG  AAACTATGAG ACTGATACCG AACCGTCATG TAATCATCAT AGTAACCAGT 3360
GGTTCAATGT GAATTTTAAA ATGGAATTAT TGGTATTGTT ATAGGAAATA AATAGAGCTG 3420
TAAATGAAAA AAAAAAAAA AA                                          3442
```

FIG. 2C

Glu 100μM
FIG. 11
FIG. 12
| | A | B | C |
|---|---|---|---|
| Na+ | 0 mM | | |
| K+ | 98 mM | | |
| Glu | 10 mM | 0 mM | 10 mM |
+30 mV 
-10 mV
-60 mV 
-100 mV 
10 nA
1 MIN
FIG. 13

1

COMPOSITIONS CORRESPONDING TO A HIGH-AFFINITY GLUTAMATE TRANSPORTER MOLECULE AND METHODS FOR MAKING AND USING SAME

This application is a continuation of Ser. No. 08/194,719, filed Feb. 10, 1994, now abandoned, which is itself a continuation-in-part of Ser. No. 07/965,676 filed Oct. 19, 1992, now abandoned.

FIELD OF THE INVENTION

This invention relates generally to compositions corresponding to a high affinity glutamate transporter protein of the brain and other organs. High affinity glutamate transporter proteins are involved in terminating the post synaptic action of glutamate in glutamatergic neurons and in active absorption of glutamate in epithelial cells of kidney and intestine. Glutamate is a major excitatory neurotransmitter in the brain. The high affinity glutamate transporter protein rapidly removes glutamate from the synaptic cleft.

BACKGROUND OF THE INVENTION

Membrane vesicle studies of neurons, glial cells, and epithelial cells have suggested the existence of two types of transport systems of glutamate across cellular membranes. One type of transport system exhibits high affinity for glutamate with a Michaelis constant (Km) of 2 to 50 µM. This type is known as the high affinity glutamate transport system. The other type of transport system exhibits low affinity for glutamate transport with a Km value of >100 µM. This system is known as the low affinity glutamate transport system.

Studies on brain, intestine and kidney suggest that high affinity glutamate transport systems have a characteristic stereo specificity with preference for L-glutamate and D-/L-aspartate. The studies further suggest that the uptake and transport of glutamate is sodium but not chloride dependent and is activated by intracellular potassium.

The studies suggest that the transport of glutamate is electrogenic. Glutamate is co-transported with two sodium ions and one hydrogen ion, and counter-transported with one potassium ion or, alternatively, co-transported with two sodium ions and counter-transported with one potassium ion and one hydroxyl ion.

Aberrant high affinity glutamate transport functions have been associated with several neuro degenerative diseases such as amyotrophic lateral sclerosis (ALS), Huntington's Disease and Alzheimer's Disease.

With respect to ALS, the neurons of the affected areas of the cerebral cortex and the spinal cord exhibit a defect in the high affinity glutamate transport function. The defect could lead to neurotoxic levels of extracellular glutamate. This can result in a persistent over-stimulation of nerve cells followed by the death of neurons, probably due to excessive calcium ion influx through N-methyl-D-aspartate receptor channels.

A number of pathologic conditions may lead to high levels of extracellular potassium concentrations. The pathologic conditions which may lead to high levels of extracellular potassium concentration include, without limitation, epileptic seisures, ischemia after a stroke, or anoxia caused by perinatal asphyxia. High concentrations of extracellular potassium may cause non-vesicular release of glutamate through reversed high affinity glutamate transport. The high extracellular glutamate concentration can lead to neurotoxic levels and neuronal death.

Efforts to isolate chemicals which enhance or inhibit the activity of high affinity glutamate transport proteins has been hampered by the inability to characterize these proteins. Although certain features of the proteins are known, nucleic acid and amino acid sequences corresponding to the proteins have not been isolated.

In this application, the term "corresponding" means, with respect to nucleic acids, nucleic acids having nucleotide sequences which are substantially homologous with or complementary to a particular sequence of nucleic acid. As between nucleic acid and peptides, "corresponding" refers to amino acids of a peptide in an order derived from the sequence of a nucleic acid or its complement or, the sequences of a nucleic acid or its complement in an order derived from the sequence of amino acids.

The term "non-naturally occurring" with respect to nucleic acid refers to a portion of genomic nucleic acid, cDNA, semisynthetic nucleic acid, or synthetic origin nucleic acid which, by virtue of its origin or manipulation: (1) is not associated with all of a nucleic acid with which it is associated in nature, (2) is linked to a nucleic acid or other chemical agent other than that to which it is linked to in nature.

With respect to peptides and proteins, "non-naturally occurring" refers to a portion of a large naturally occurring peptide or protein, or semi-synthetic or synthetic peptide, which by virtue of its origin or manipulation: (1) is not associated with all of a peptide with which it is associated in nature, (2) is linked to peptides, functional groups or chemical agents other than that to which it is linked in nature, or (3) does not occur in nature.

The term "highly conserved" refers to areas of a nucleic acid or peptides which are similar or identical between species.

The term "excitatory" is used in the sense of associated with the function of neurons. The term "carrier" refers to transporter functions.

The term "dicarboxylic aminoaciduria" is a pathological condition characterized by increased urinary excretion of glutamate and aspartate. This condition is often associated with neurological and developmental abnormalities. This condition is believed to be caused by inborn defects in high-affinity glutamate transporter which mediate net absorption of glutamate and aspartate across epithelial cells. As used herein, a defect in the high affinity glutamate transport refers to a non-functional protein and/or the gene which codes the protein or a complete absence of the protein and/or the gene which codes the protein.

SUMMARY OF THE INVENTION

Embodiments of the present invention are directed to compositions exhibiting high affinity to glutamate and capable of transporting glutamate, in appropriate in vivo systems, across cellular membranes, and methods for making and using the compositions. One embodiment of the present invention features a composition of matter comprising a non-naturally occurring excitatory amino acid carrier protein. The protein has high affinity for glutamate. As used herein, "high affinity" refers to a Michaelis constant or affinity constant between approximately 2 to 50 µM.

Preferably, the protein has an affinity constant between 10–30µM. The human excitatory amino acid carrier protein has a Km of 30.±3.0 µM. The rabbit excitatory amino acid carrier protein has a Km of 12.2 µM.

The excitatory amino acid carrier protein is highly expressed in neuronal structures in the cerebral cortex, cerebellum, hippocampus, and brain stem. It is also abundantly expressed in the kidney and small intestine, and to a lesser degree in the liver and heart. The protein is associated with high affinity glutamate transport in vivo.

Preferably, the carrier protein has an amino acid sequence corresponding to a nucleic acid sequence within Seq. ID No.1 or Seq. ID No. 2. The sequence of Seq. ID No. 1 and 2 are set forth in the sequence listings of this application.

The sequence of Seq. ID No. 1 represents 1611 nucleotides of a nucleic acid of approximately 3.5 Kb in length. The sequence associated with the carrier protein is found from nucleotides 40 to 1611.

The carrier protein corresponding to Seq. ID No. 1 has an amino acid sequence as set forth in Seq. ID No. 2. The amino acid sequence of Seq. ID No. 2 is set forth in the sequence listings of this application. Seq. ID No. 2 is a putative sequence derived from the nucleic acid sequence. The deduced protein has 524 amino acids.

The sequence of Seq. ID No. 3 is derived from rabbit and is 3,442 nucleotides in length. The sequence associated with the carrier protein is found from nucleotides 177 to 1749. Preferably, the carrier protein corresponds to the coding sequence within the sequence sections 177 to 1749 of Seq. ID No. 3.

Preferably, the carrier protein has amino acid sequence as set forth in Seq. ID No. 4. The amino acid sequence of Seq. ID No. 2 is also set forth in the sequence listings of this application. Seq. ID No. 2 is a putative amino acid derived from the nucleic acid sequence. The deduced protein has 524 amino acids.

Small variations in the nucleic acid sequences and the corresponding amino acids are anticipated, particularly when comparing sequences, for molecules having identical characteristics and features, derived from different species. The membrane spanning regions are often the most conserved regions whereas hydrophilic (intra or extracellular) regions may be less conserved in membrane transport proteins.

The sequences derived from humans and rabbit may be used as probes to identify and characterize similar sequences derived from any other eukaryotic species.

One embodiment of the present invention features, as a composition of matter, a nucleic acid corresponding to a protein which protein has high affinity for glutamate. The protein is capable of transporting glutamate across cellular membranes in vivo.

The sequence derived from human sources, Seq. ID No. 1, codes for the protein from nucleotides 40 to 1611.

Preferably, the nucleic acid has a sequence which corresponds to a sequence within Seq. ID No. 1 or 3. The sequence derived from rabbit, Seq. ID No. 3 codes for the protein from nucleotide 177 to 1749 of Seq. ID No. 3. Preferably, the nucleic acid has a sequence which corresponds to one or more of the highly conserved coding regions from nucleotides 40 to 1611 of Seq. ID No. 1 or nucleotides 177 to 1749 of Seq. ID No. 3.

The compositions of the present invention are useful for altering the features of neurons. The excitatory amino acid carrier can be placed into cells to alter the uptake of glutamate. Such modified non-naturally occurring cells may have the enhanced ability to take up glutamate.

Anti-sense nucleic acids which are complementary to the nucleic acid sequence of excitatory amino acid carrier protein can be used to down regulate the expression of the gene encoding for the protein.

The nucleic acid sequences can be placed in a host cell capable of expressing the nucleic acid to produce substantially pure quantities of excitatory amino acid carrier protein.

One embodiment of the present invention features a method of identifying chemicals capable of interacting with an excitatory amino acid carrier protein exhibiting high affinity for glutamate. The method comprises the steps of contacting cell with a chemical. The cell has a non-naturally occurring nucleic acid encoding for an excitatory amino acid carrier protein. The excitatory amino acid carrier protein has high affinity for glutamate and is capable of transporting glutamate across cellular membranes. The method further comprises the step of monitoring the cells for a change in the uptake or outflow of glutamate or molecules associated with the movement of glutamate. The changes suggest an interaction with the protein, Preferably, the excitatory amino acid carrier protein shows reversed glutamate transport. In a number of pathological conditions such as ischemia and anoxia, the extracellular potassium concentration is elevated. This elevation has been associated with the reversed transport of glutamate by high affinity glutamate transporters. The reversed transport of glutamate may be a major cause of the elevation of extracellular glutamate which leads to neuronal death.

Preferably, the nucleic acid has a sequence corresponding to a sequence within Seq. ID No. 1 or Seq. ID No. 3. More preferably, the nucleic acid corresponds to a sequence from nucleotides 40 to 1611 of Seq. ID No. 1 or from 177 to 1749 of Seq. ID No. 3. Preferably, the nucleic acid has a sequence corresponding to highly conserved coding regions from nucleotides 40 to 1600 of Seq. ID No. 1 or nucleotides 177 to 1749 of Seq. ID No. 3.

Preferably, the protein has an amino acid sequence which corresponds to an amino acid sequence in Seq. ID No. 2 or Seq. ID No. 4. Most preferably, the protein corresponds to an amino acid sequence in. Seq. ID No. 2 derived from humans.

Any prokaryotic or eukaryotic cell which expresses the excitatory amino acid carrier protein in the plasma membrane can be monitored for the uptake of glutamate and sodium and the outflow of potassium. The cell may also be monitored for electrical activity indicative of the uptake or outflow of the charged species from the cell.

The present method is suitable for identifying enhancers of the carrier protein and inhibitors of the carrier protein. Embodiments directed to identifying chemicals which interact with the carrier protein are useful for screening chemicals for biological activity and as biosensors.

One embodiment of the present invention features a method of altering the uptake or release of glutamate by a cell. The method comprises a step of incorporating an excitatory amino acid carrier protein into the cell membrane, which carrier protein is capable of transporting glutamate across cellular membranes.

Preferably, the cell is a neuron. In one embodiment of the present invention the excitatory amino acid carrier protein is encoded on a nucleic acid, which nucleic acid is placed in the neuron, and is capable of being expressed. The neuron expresses the nucleic acid to make the carrier protein which carrier protein is incorporated into the cell membrane.

Embodiments of the present invention feature a nucleic acid having a sequence corresponding to a sequence within Seq. ID No. 1 or Seq. ID No. 3. Preferably, the sequence corresponds to highly conserved coding region from nucleotides 40 to 1611 of Seq. ID No. 1 or 177 to 1749 of Seq. ID No. 3.

Preferably, the carrier protein has amino acid sequence corresponding to a sequence within Seq. ID No. 2 or Seq. ID No. 4.

A further embodiment of the present invention features a method of treating dicarboxylic aminoaciduria. The method comprises the step of incorporating into the cell wall of a cell, which cell has a defective excitatory amino acid carrier protein or gene, an excitatory amino acid carrier protein. The excitatory amino acid carrier protein functions to transport glutamate across the cell wall.

A further embodiment of the present invention features a method of detecting defects in the gene coding an excitatory amino acid carrier protein or detecting defects in the protein expressed. The method comprises comparing a first nucleic acid sequence, or a first amino acid sequence of a protein, with a second nucleic acid sequence for the excitatory amino acid carrier protein or with a second amino acid sequence for the excitatory amino acid carrier protein. As used herein, "comparing" means identifying mismatches or variances by sequencing or by hybridizing to a known sequence, or isolation proteins and genes and comparing such proteins and genes in a functional setting. The variances between the first sequence and the second sequence are indicative of a defect in the nucleic acid or protein. Preferably, the second nucleic acid is selected from a sequence with Seq. ID No. 1 or Seq. ID No. 3. The second amino acid sequence is selected from a sequence within Seq. ID No. 2 or 4. The first nucleic acid is preferably derived from human chromosome 9.

Embodiments of the present invention directed to altering the uptake of glutamate by neurons may have applications for neuronal disorders associated with a defect in glutamate transport. Such neuronal disorders are associated by way of example, without limitation, ALS, Huntington's disease and Alzheimer's disease. Embodiments of the present invention directed to the uptake of glutamate by neurons may also have applications for other pathologic conditions. Such conditions are, by way of example, without limitation, epilepsy, depression, ischemia after stroke, or anoxia caused by perinatal asphyxia.

Other features and advantages of the present invention will be apparent from the following description which, by way of illustration, shows preferred embodiments of the present invention and the principles thereof and what is now considered to be the best mode to apply these principles.

BRIEF DESCRIPTION OF THE DRAWINGS

FIGS. 1a–c are a depiction of Seq. ID No. 1 with the corresponding amino acid sequence from nucleotide 40 to 1611;

FIG. 2 is a depiction of Seq. ID No. 3 with the corresponding amino acid sequence from nucleotide 177 to 1749;

FIG. 11 is a graphical description of electrical activity of Xenopus laevis oocytes having an exogenous nucleic acid for the excitatory amino acid carrier protein, in response to glutamate;

FIG. 12 is a graphical description of electrical activity of Xenopus laevis oocytes having an exogenous nucleic acid for the excitatory amino acid carrier protein, in response to high potassium ion; and FIG. 13 is a graphical description of electrical activity of Xenopus laevis oocytes having an exogenous nucleic acid for the excitatory amino acid carrier protein, in response to high potassium ion, at different voltages.

DETAILED DESCRIPTION

The present invention will be described as an excitatory amino acid carrier protein having high affinity for glutamate. The excitatory amino acid carrier protein is derived from rabbit intestine. The excitatory amino acid carrier protein derived from rabbit is anticipated to correspond closely to excitatory amino acid carrier proteins of humans and other species. Thus, the present invention should not be construed as limited to a particular sequence or derived from a particular organism.

Figure 3:
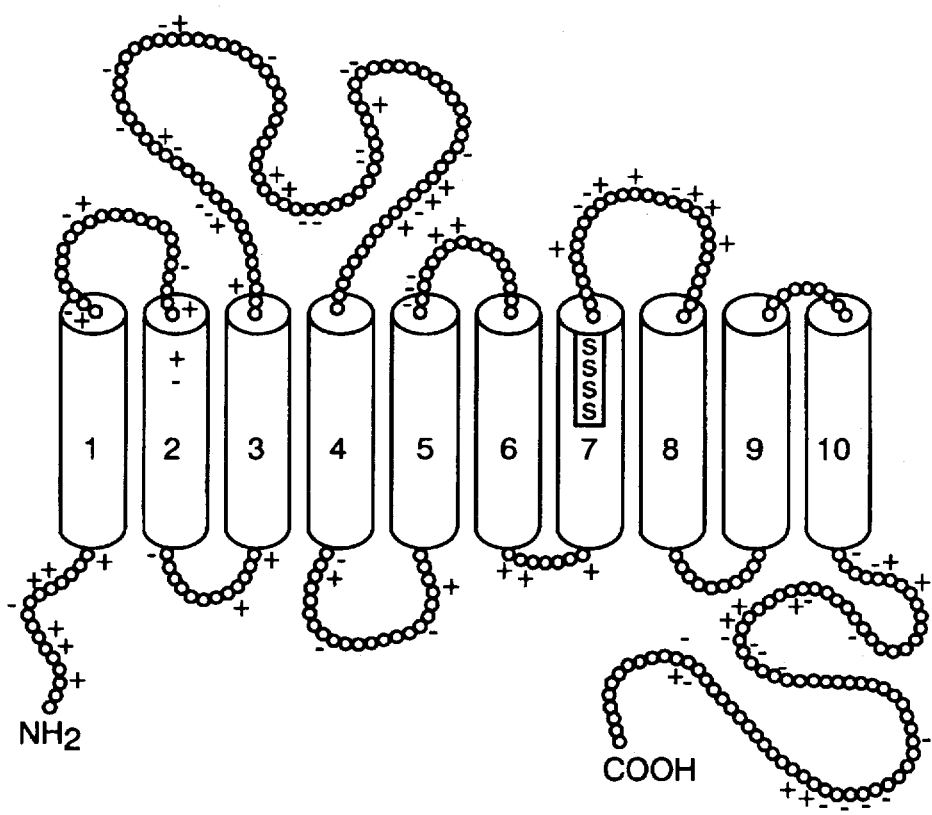
FIGS. 3a and 3b are a topological model of the excitatory amino acid carrier protein derived from rabbit or human sources within a cell membrane.

Turning now to FIGS. 1 and 3, the carrier protein is encoded by a 3,442 base nucleic acid sequence. The sequence derived from humans is depicted in FIG. 1 and the sequence derived from rabbit is depicted in FIG. 3. These cDNAs encode for proteins which consists of 524 amino acids and have a predicted molecular weight of 57 kda. From the deduced amino acid sequence, ten putative transmembrane regions can be identified.

A topological model for these excitatory amino acid carrier proteins are illustrated in FIG. 3.

The excitatory amino acid carrier proteins represented by FIG. 3 have several general similarities. Because of the large hydrophobic stretch towards the C-terminus (residues 357–444), a model with ten different putative transmembrane domains could be constructed. The end terminal part of the excitatory amino acid carrier is hydrophilic and lacks a typical signal peptide. The protein exhibits three potential N-glycosylation sites at Asn 43, 178 and 195. The carrier protein exhibits nine consensus sequences for protein kinase C (PKC)—dependent phosphorylation scattered throughout the sequence.

The cDNA sequence derived from rabbit intestine and the cDNA sequence derived from human sources are very similar, with greater than 90% sequence identity. Other mammalian DNA encoding for the excitatory amino acid carrier can be readily isolated using selected sequences of the cDNA presented in this application as probes to identify or isolate corresponding sequences.

Predicted membrane spanning regions of excitatory amino acid carrier protein are shown by lines below the sequences. Numbers above the sequences refer to the amino acid sequence of the excitatory amino acid carrier protein. The bold line above the sequences indicates the serine rich regions.

A cluster of conserved serine residues in membrane spanning region 7, corresponding to sequences 331–334 of Seq. ID No. 2 or 4, may represent a functional motif. Similar serine rich regions have been identified in the ligand binding sites of cell surface receptors. Such similar serine rich regions typically are located in transmembrane domains one to two helical turns away from the outer surface of the plasma membrane and are involved in substrate binding through the formation of hydrogen bonds to biogenic amines (e.g., acetycholine, norepinephrine, dopamine, serotonin and histame).

In the excitatory amino acid carrier protein of the present invention, the serine residues, may serve as hydrogen donors or acceptors, and may facilitate substrate binding through the formation of hydrogen bonds to a substrate carboxylate group.

Figure 4:
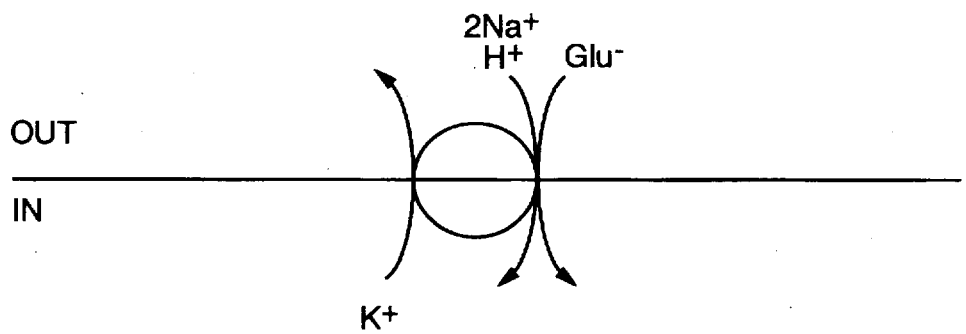
FIG. 4 is a schematic model of the transport of glutamate across a cell membrane via a excitatory amino acid carrier protein.

FIG. 4 depicts schematically a model system for the transport of glutamate from the outside to the inside of the cell via the excitatory amino acid carrier protein. Sodium ion concentration is 96 mM and potassium ion concentration is 2 mM on the outside of the cell. Glutamate is co-transported with two sodium ions and one hydrogen ion and co-transported with one potassium ion or, alternatively, co-transported with two sodium ions, and counter-transported with one potassium ion and one hydroxyl ion.

Figure 5:
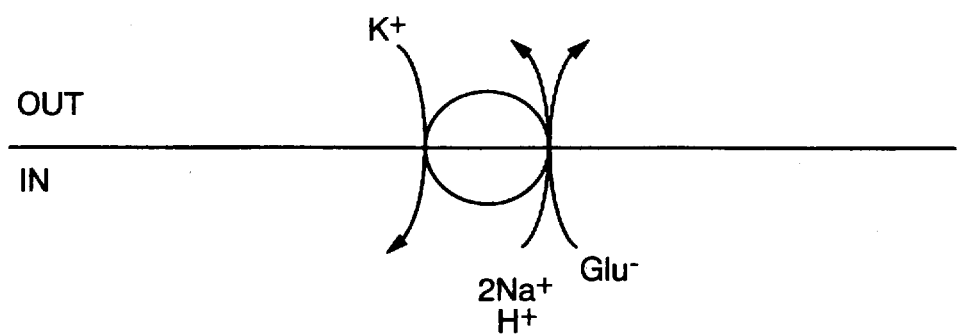
FIG. 5 is a schematic model of the reverse transport of glutamate across a cell membrane.

FIG. 5 depicts schematically a model system for the reversed transport of glutamate, from the inside to the outside of a cell. Reversed transport is believed to occur during conditions of high external potassium ion concentrations. High external potassium ion concentrations occur during several pathologic conditions such as epileptic seizures, ischemia after stroke or anoxia caused by perinatal asphyxia.

The practice of the present invention will employ, unless otherwise indicated, conventional techniques of chemistry, molecular biology, microbiology, recombinant DNA, and immunology, which are within the skill of the art. Such techniques are explained fully in the literature. See e.g., Sambrook, Fitsch & Maniatis, Molecular Cloning; *A Laboratory Manual* (1989); DNA Cloning, Volumes I and II (D. N Glover ed. 1985); Oligonucleotide Synthesis (M. J. Gait ed, 1984); Nucleic Acid Hybridization (B. D. Hames & S. J. Higgins eds. 1984); the series, Methods in Enzymology (Academic Press, Inc.), particularly Vol. 154 and Vol. 155 (Wu and Grossman, eds.).

The examples further describe preferred embodiments. Example 1 describes the isolation of the excitatory amino acid carrier protein derived from rabbit intestine.

EXAMPLE 1

RNA was extracted from jejunum mucosal scrapes of female rabbits (New Zealand White) by the guanidinium isothiocyanate method using cesium-trifluoroacetic acid (Pharmacia). Poly(A)$^+$RNA was isolated and injected into collagenase-treated and manually-defolliculated *Xenopus laevis* oocytes. Size-fractionation of rabbit jejunum poly(A)$^+$RNA using preparative gel electrophoresis and injection of fractions into oocytes showed peak stimulation of glutamate uptake by an RNA in the size-range of 2.4–4.4 kb. Size-fractionation of rabbit jejunum poly(A)$^+$RNA using preparative gel electrophoresis was performed in accordance with Hediger U.S. Pat. No. 4,479,861.

A directional cDNA library was constructed from this size-range using the SuperScript Plasmid system (GibcoBRL, MD). cDNA was ligated into the NotI and SalI sites of the expression vector pSPORT 1 (GibcoBRL) and electroporated into ElectroMax DH10B cells (GibcoBRL).

Plasmid DNA was in vitro transcribed from pools of 300–400 clones and the resulting cRNA injected into oocytes. A pool was identified which induced the uptake of glutamate 12-fold greater than water-injected controls. This pool was sequentially subdivided and in vitro transcribed until a single preferred clone was identified. The preferred clone was able to express an excitatory amino acid carrier protein 1,300-fold above water injected controls.

All uptakes in this and the following figures were performed with 6–8 oocytes, 3 days after injection. Incubation was for 1 hour in 750 µl standard uptake solution (100 mM NaCl, 2 mM KCl, 1 mM MgCl$_2$, 1 mM CaCl$_2$, 10 mM Hepes, 5 mM Tris pH 7.4) and 50 µM $^{14}$C-L-glutamate. For the sodium-free medium, sodium chloride was replaced by Choline-chloride. RNA-injected oocytes were injected with 25 ng cRNA in 50 nl.

Figure 6A:
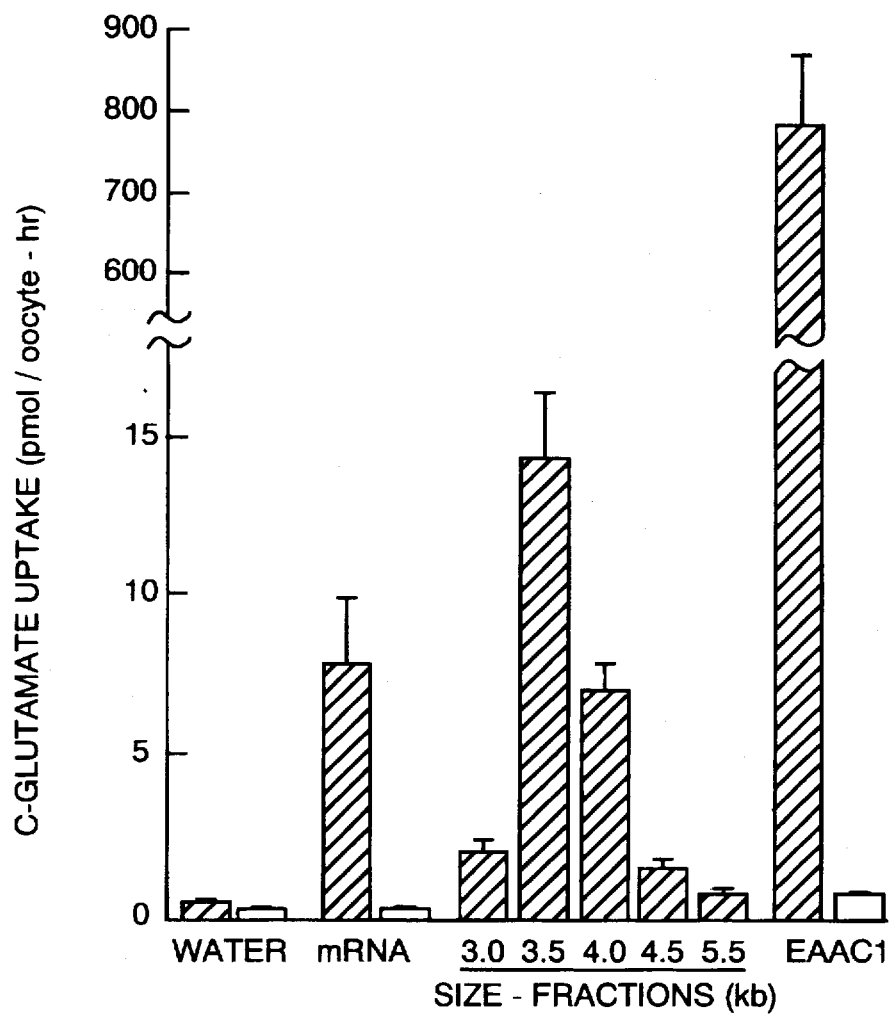
FIGS. 6a and 6b depict in bar graph form the uptake of $^{14}$C-Glutamate by oocytes injected with $H_2O$ or RNA.

Turning now to FIG. 6, results are depicted in bar graph form for water, mRNA size fractions of 3.0, 3.5, 4.0, 4.5 and 5.5 kilobases, and in vitro transcribed cRNA corresponding to Seq. ID. No. 3.

Figure 6B:
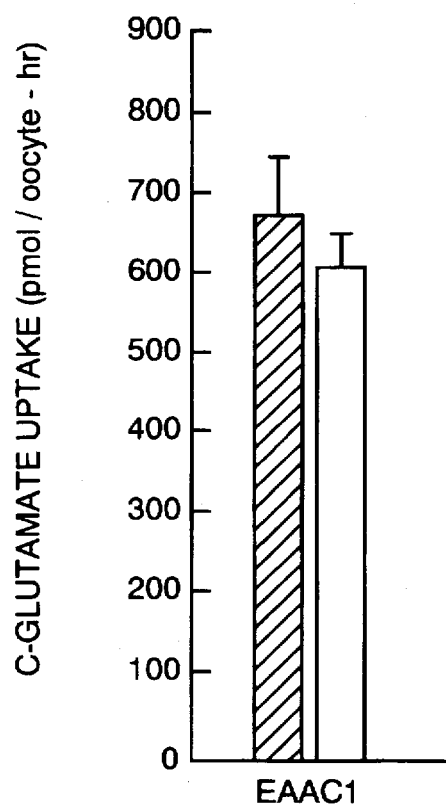

Each column represents the mean±s.e.m. (n=6–8 oocytes). The vertical bars give the standard error. Hatched columns indicate the uptake values in the presence of Na$^+$ (100 mM) in medium. Open columns show the uptakes in Na$^+$-free medium in which Na$^+$ is replaced by choline $^+$. The uptake of the preferred cRNA-injected oocytes showed the complete Na$^+$-dependency as did total poly(A)$^+$RNA-injected oocytes. FIG. 6(b) illustrates the uptake $^{14}$C-L-glutamate by cRNA injected oocytes in the absence of chloride ion. The solutions described above were modified to the extent that acetate ion was substituted for chloride ion.

The hatched column indicates $^{14}$C-L-glutamate uptake into the preferred cRNA-injected oocytes measured in the standard uptake solution ([Cl−]=106 mM). The open column shows the uptake in the absence of Cl$^-$ (Cl$^-$ was replaced by acetate). The uptake did not show significant dependence on Cl concentration in the medium.

EXAMPLE 2

Example 2 describes the sequence of cDNA associated with the clone exhibiting high expression of excitatory amino acid carrier protein, referred to herein as EAAC1 cDNA.

EAAC1 cDNA or cDNA fragments produced by internal restriction sites were subcloned into pBluescript II (Stratagene) and were completely sequenced in both directions using the Sequenase 2.0 DNA sequencing kit (USB, OH). Synthetic oligonucleotide primers were used to complete sequencing. FIG. 1 and FIG. 2 describe nucleic acid sequences presented in Seq. ID No. 1 and Seq. ID No. 3, and amino acid sequences presented in Seq. ID No. 2 and Seq. ID No. 4.

Turning now to FIG. 2, the AUG initiation codon at position 177 matches the Kozak consensus initiation sequence [GCC(A/G)CCAUGG]. The putative transmembrane domains predicted with Eisenberg's algorithm are marked by lines numbered 1–10. Potential N-linked glycosylaton sites (Ash 43, 85, 178 and 195) and polyadenylation sequences (AATAAA) at position 2,487 and at 3,407 are underlined. Potential PKC-dependent phosphorylation sites (S/T-X-K/R) are located at residues 11, 87, 115, 121, 164, 175, 247, 340 and 466.

FIG. 3 depicts a membrane model of an excitatory amino acid carrier protein derived from human and rabbit sources.

Individual amino acid residues are shown as circles. Putative transmembrane regions are depicted as cylinders. Strongly charged amino acids (arginine, lysine, glutamic acid, and aspartic acid) are indicated by their charges.

EXAMPLE 3

Example 3 illustrates the expression of the excitatory amino acid carrier protein in various tissues using a Northern analysis. Poly(A)+RNA was prepared as described in Example 1N Poly(A)+R A (3 µg) or total RNA (10 µg; hippocampus) was separated on 1% formaldehyde agarose gel, and blotted onto nitrocellulose filters (Schleicher & Schuell, NH). The nucleic acid associated with the carrier protein was excised from pSPORT1 and labelled with $^{32}$P using QuickPrime kit (Pharmacia). Hybridization was performed for 16 hours at 42° C. (50% formamide). Washing was done in 0.1×SSC/0.1% SDS at 65° C.

A search of protein sequence databases (June, 1992) revealed weak but significant sequence similarities between the excitatory amino acid carrier protein and prokaryotic transporters. We found the excitatory amino acid carrier protein to have 30% identity to the E. coli GltP proton/glutamate-aspartate symporter and 27% identity to the DctA dicarboxylate transporter from Rhizobium meliloti DctA. There was no significant homology between the excitatory amino acid carrier protein and the E. coli sodium/glutamate transporter GltS, the sodium/glucose transporter and related transporters or to sodium- and chloride-dependent transporters of GABA, norepinephrine, dopamine, serotonin, L-glycine and L-proline. The similarities of the GltP, DctA and the excitatory amino acid carrier protein nucleic acid sequences, with the absence of a significant sequence homology to sodium and chloride-dependent neurotransmitter transporters of to any other published sequence, suggest that the excitatory amino acid carrier protein, GltP and DctA define a new and distinct protein superfamily.

These homologies could be used to design PCR primers, to amplify nucleic acids corresponding to other transporter proteins. By way of example, without limitation, dicarboxylate transporters and glutamine transporters may be isolated using PCR primers. An example of a dicarboxylate transporter is neuronal α-ketoglutarate transporter. α-ketoglutarate is a precursor of glutamate in neuronal synthesis. Glutamine is also a precursor of glutamate in neuronal synthesis. The excitatory amino acid carrier protein of Seq. ID No. 4 has slight activity for glutamine transport, suggesting the carrier protein of Seq. ID No. 4 and glutamine transporters have similar structures.

By way of further example, high affinity glutamate transporters from other tissues, such as glial high affinity glutamate transporter, and low affinity glutamate transporters from the brain and other tissues, may be isolated using PCR primers.

Highly conserved regions in the excitatory amino acid carrier nucleic acid which may be suitable for designing PCR primers and for amplifying such related transporter sequences are, for example, nucleotides 324 to 338 and 354 to 418 of Seq. ID No. 1 or 3.

A high stringency Northern analysis of RNA from rabbit tissues was performed using $^{32}$P-labelled cDNA having a sequence corresponding to Seq. ID No. 3. The rabbit tissues evaluated were liver, heart, colon, duodenum, jejunum, ileum, kidney superficial cortex, kidney cortex, kidney outer medulla, skeletal muscle, spleen, lung, cerebral cortex, cerebellum, brain stem and hippocampus. A strong 3.5 kb band was detected in duodenum, jejunum, ileum, kidney superficial cortex and remaining cortex, and brain samples, particularly the cerebral cortex. A weak band of identical size was present in liver and heart. An additional 2.5 kb band of varying extent was detected in all positive tissues except brain. The band in hippocampus was slightly shifted to lower size. The difference in the band sizes is probably because more total RNA was loaded on the gel than poly(A)+RNA (10 µg of total RNA for hippocampus and 3 µg of poly(A)+RNA for all other tissues).

EXAMPLE 4

Example 4 illustrates the expression of the excitatory amino acid carrier protein in various tissues using a polymerase chain reaction (PCR) analysisN First strand cD A was synthesized from 0.5 µg of poly(A)+RNA from cerebral cortex, cerebellum and jejunum and 2.5 µg of total RNA from hippocampus by using an oligo $dT_{12-18}$ as a primer. Subsequently, a sense primer (5'-GACAGATTCTGGTGGATTTCTTC-3'), and an anti-sense primer (5'-ATACTAGTCTGTACATGAAAAAG-3') corresponding to nucleotides 874–896 and 2,062–2,084 of Seq. ID No. 3, respectively, were used to amplify 1% of the products from the reverse transcription reaction or 0.5 pg of cDNA encoding for the excitatory amino acid carrier, subcloned in pBluescript II, for 30 cycles (10 sec at 92° C., 1 min at 55° C., 2 min at 72° C.). PCR products were separated by electrophoresis through a 1% agarose gel and stained with ethidium bromide.

Gel analysis of the PCR products of first strand cDNA from cerebral cortex, cerebellum and hippocampus suggests the same size of amplification products as those detected in jejunum and obtained from cDNA encoding for the excitatory amino acid carrier protein.

EXAMPLE 5

Example 5 illustrates detection of excitatory amino acid carrier protein expression in situ for various tissues. In situ hybridization of rabbit jejunum and brain tissues (hippocampus, cerebellum and cerebral cortex) was performed as described in Kanai, Y. et al, Am. J. Physiol. (in press)(1992). To briefly summarize, following perfusion fixation with 4% paraformaldehyde, hippocampus, cerebellum and cerebral cortex were removed and post-fixed in 4% paraformaldehyde. Jejunum was taken under deep anesthesia and fixed by immersing in 4% paraformaldehyde. Two serial cryosections (9 µm for jejunum and 18 µm for brain tissues) were prepared for use in in situ hybridization.

$^{35}$S-labelled sense and anti-sense RNA probes were synthesized from a subclone (646-2783 StuI-StuI EAAC1 fragment ligated into the pBluescript II EcoRV site) after linearization with EcoRI or HindIII, using T7 or T3 RNA polymerase, respectively. RNA probes were degraded by partial hydrolysis for 40 min. After being treated with proteinase K (2 µg/ml, 7.5 min) and acetylated with acetic anhydride, cryosections were hybridized with probes at 50° C. overnight in the hybridization solution (50% formamide). Sections were stringently washed in 5×SSC for 30 min. at 50° C. and then with 50% formamide and 2×SSC for 20 min. The sections were treated with RNase A (40 µg/ml) and RNase T1 (2 µg/ml) at 37° C. for 30 min.

Air-dried slides were dipped into Kodak NTB2 emulsion and developed 5–10 days later. Some brain and jejunum slides were counter-stained with cresylviolet and hematoxylin-eosin.

Microscopic examination of the hippocampal formation sample indicated that the anti-sense cRNA probe corresponding to the excitatory amino acid carrier protein strongly hybridized to the pyramidal layer of hippocampus and granular layer of the dentate gyrus layer 5. Hybridization in the pyramidal layer extended into the hilus and subiculum.

Microscopic examination of the folia of cerebellum revealed a dense hybridization pattern in the granule cell layer, although at a lesser extent compared with that of the pyramidal layer.

Microscopic examination of the cerebral cortex samples revealed hybridization in cells in layer II–VI. The signal was not detected in the deep white matter.

Microscopic examination of jejunum samples revealed a strong hybridization signal in epithelial cells. Grains were not detected in the submucosal layer or in the muscle layer.

Control experiments using sense cRNA corresponding to the excitatory amino acid carrier protein as a probe were found to show only background levels of hybridization.

Similarly, using rat antisense cRNA probe derived from moderate to high stringency screening of a rat brain cDNA library using rabbit excitatory amino acid carrier cDNA as a probe, high to medium levels of mRNA expression of the excitatory amino acid carrier protein were detected in neurons distributed heterogeneously throughout the brain and spinal cord. In the forebrain a strong hybridization signal was prominent in cortical neurons at all rostrocaudal levels and was particularly dense over neurons in layer 5. A robust signal was also seen in dentate granule cells and pyramidal cells of the hippocampus. Most thalamic nuclei including neurons of the ventrobasal complex expressed high mRNA expression. However, expression was not detected within the habenular complex and was similarly absent from most regions of the hypothalamus.

The most conspicuous group of labeled neurons in the midbrain was seen in the deep layers of the superior colliculus strongly labeled cells were present but more sparsely distributed to pretectal and ventral midbrain regions. Dense silver grains were found over pyramidal neurons in the cerebellum and over neurons of the deep cerebellar nuclei. In the spinal cord expression of the excitatory amino acid carrier protein was seen throughout the gray matter but was most prominent in the ventral horn in association with large alpha motor neurons. In the retina the hybridization signal was discretely concentrated over individual cells in the ganglion cell layer and more diffusely deposited in the inner nuclear layer. Some of the neuronal populations which express the excitatory amino acid carrier protein (e.g., cortical neurons) are known to use glutamate as a neurotransmitter. In some populations which express the excitatory amino acid carrier protein (thalamic neurons) glutamate is strongly suspected to be the neurotransmitter. For other populations (Purkinje cells of the cerebellum) there is no evidence that glutamate is a neurotransmitter.

EXAMPLE 6

Example 6 illustrates electrophysiological features of *Xenopus laevis* oocytes capable of expressing cRNA encoding the excitatory amino acid carrier protein.

*Xenopus laevis* oocytes were injected with cRNA (25 ng/oocyte) encoding for the excitatory amino acid carrier protein derived from rabbit as described in Example 1. Electrophysiological measurements were performed 3–4 days after injection using a conventional two-microelectrode voltage clamp method (Axoclamp-2A, Axon Instruments, CA).

Figure 7:
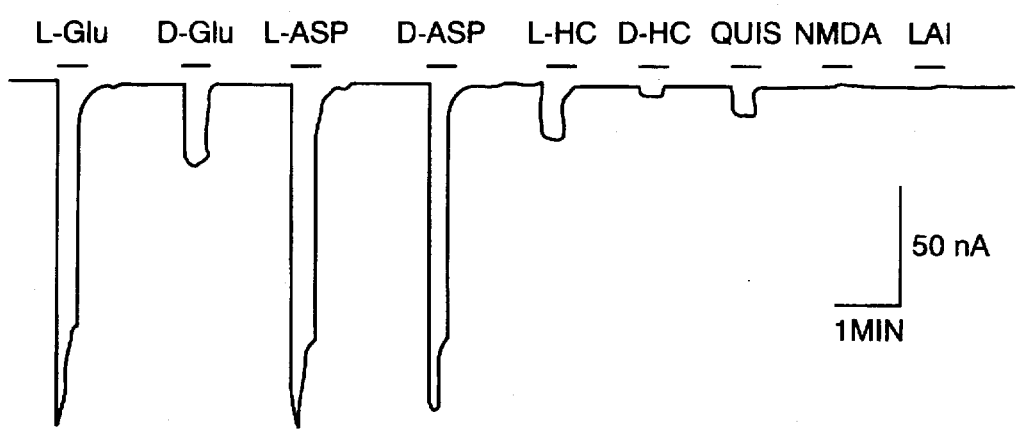
FIG. 7 is a graphical depiction of the electrical activity of Xenopus laevis oocytes having an exogenous nucleic acid for the excitatory amino acid carrier protein in response to glutamate and other compounds.

The standard bath solution (ND 96) contained 96 mM NaCl, 2 mM KCl, 1.8 mM $CaCl_2$, 1.0 mM $MgCl_2$ and 5 mM HEPES pH 7.4 The recording chamber was perfused with bath solution. Current responses of *Xenopus laevis* oocytes injected with cRNA coding for the excitatory amino acid carrier protein and fragments thereof to bath applied 100 µM substrates are illustrated in FIG. 7.

The membrane current was measured in standard bath solution (ND 96) at −60 mV holding potential. Substrates were applied at the bars. FIG. 7 depicts inward current as being downwardly directed. As used in FIG. 7, the abbreviations "L-Glu" is used for L-glutamate; "D-Glu" is used for D-glutamate; "L-Asp" is used for L-aspartate; "D-Asp" is used for D-aspartate; "L-HC" is used for L-homocysteate; "D-HC" is used for D-homocysteate; "Quis" is used for quisgualate; "NMDA" is used for N-methyl-D-aspartate; and "Kai" is used for kainate.

L-glutamate, L-aspartate and D-aspartate evoked almost the same amplitude of inward currents, while currents induced by D-glutamate and L- or D-homocysteate were small compared to L-glutamate. Glutamate receptor ligands, NMDA and kainate did not induce current. Quisgualate, however, evoked a small but significant inward current.

The uptake of $^{14}C$-L-glutamate or $^{14}C$-L-aspartate (50 µM) by cRNA injected oocytes was measured in standard uptake solution containing 1 mM of inhibitors, D-glutamate, L-aspartate and D-aspartate.

Figure 8:
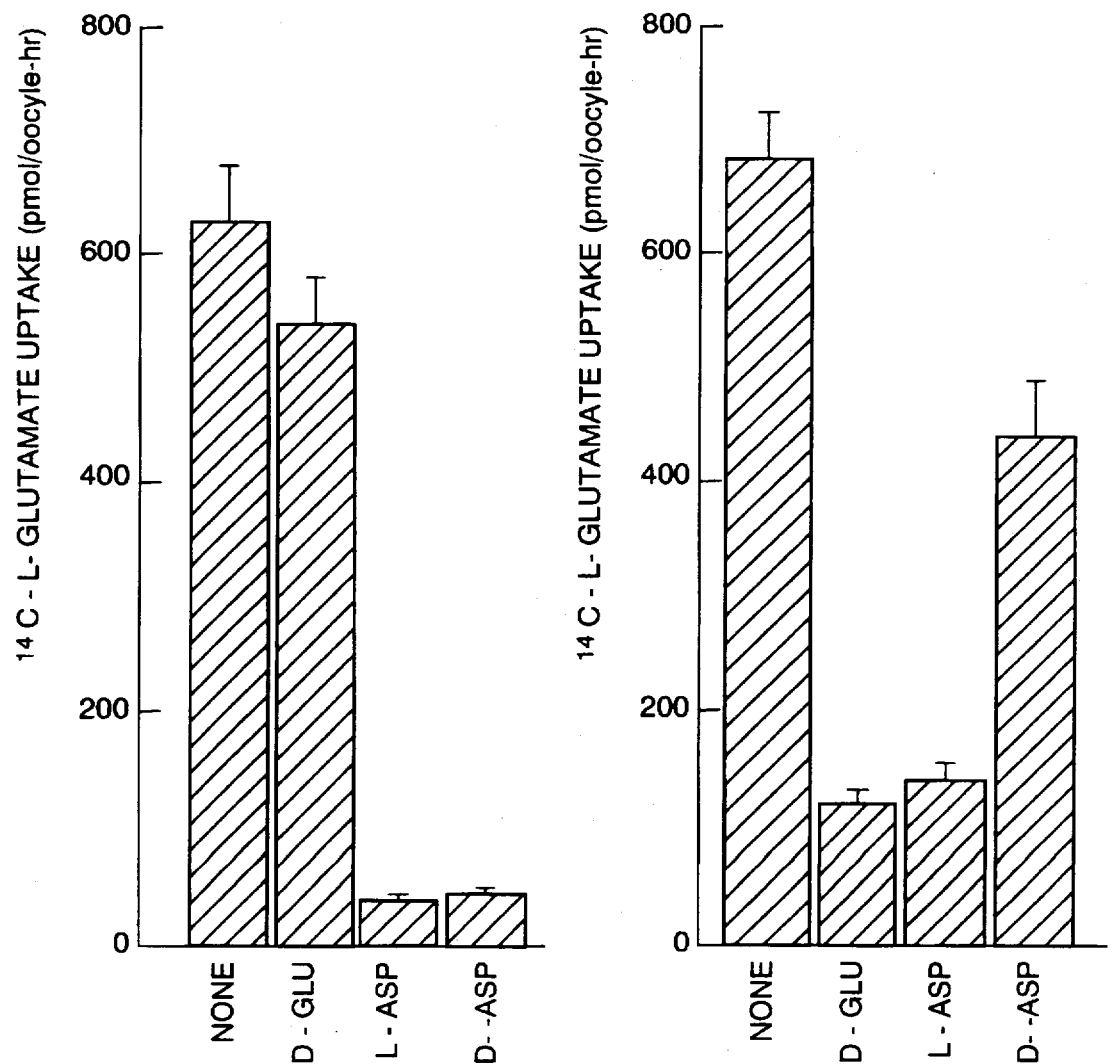
FIG. 8 is a bar graph illustration of glutamate uptake by Xenopus laevis oocytes having an exogenous nucleic acid for an excitatory amino acid carrier protein in response to inhibitory chemicals.

The results are depicted in bar graph form in FIG. 8. The abbreviations D-Glu, L-Asp and D-Asp are used for D-glutamate, L-aspartate and D-aspartate, respectively. The results suggest that L-glutamate uptake was inhibited by L-aspartate and D-aspartate. L-aspartate uptake was effectively inhibited by L-glutamate and D-aspartate. D-glutamate was not a good inhibitor of the excitatory amino acid carrier protein.

In the presence of L-glutamate, cRNA injected oocytes exhibited currents. The current was measured at different concentrations of L-glutamate.

Figure 9:
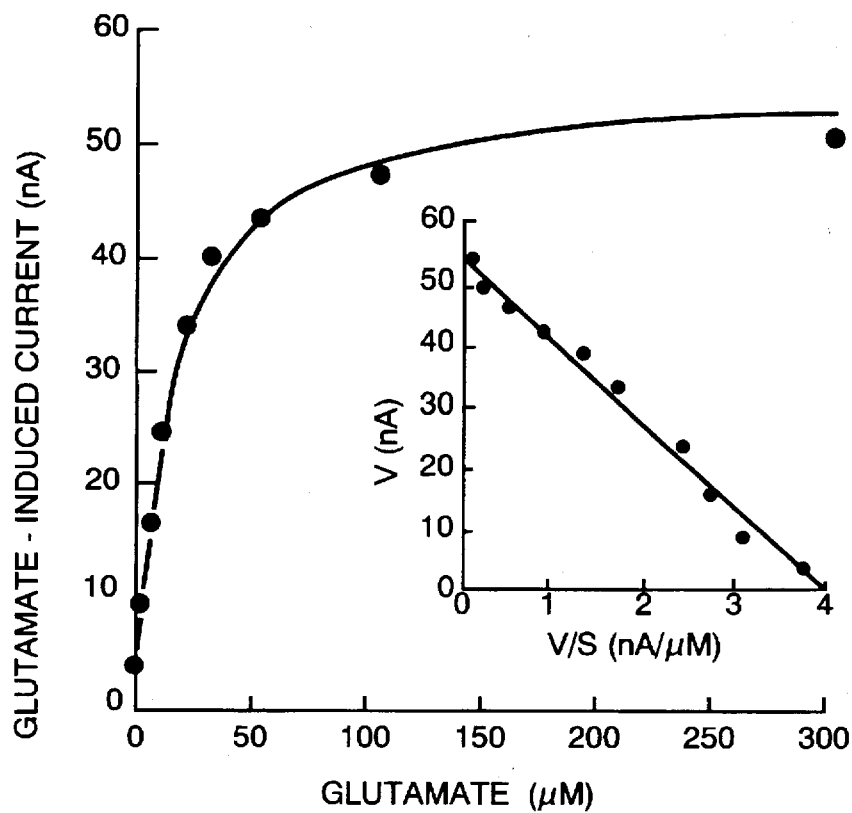
FIG. 9 is a Michaelis-Menton curve of glutamate induced current at different glutamate concentrations, with an inset illustrating the calculation of Km.

FIG. 9 graphically depicts the changes in glutamate induced current measured in nanoampere (nA) at concentrations ranging from 1 µM to 1 mM glutamate. The results were fitted to a Michaelis-Menton curve. An Eadie-Hofstee plot is depicted in the inset. The Eadie-Hofstee equation suggests a Km value of 12.2 µM. The affinity construct value is consistent with the involvement of the excitatory amino acid carrier protein in the clearance of glutamate and is comparable with the $EC_{50}$ of 19 µM of the quisgualate receptor. The quisgualate receptor is primarily responsible for fast glutamatergic neurotransmission.

In contrast, the Km value of glial glutamate transport in rat brain is 1 µM. Low Km values of around 1 µM are consistent with the role of glial glutamate transporters in maintaining the glutamate concentration of the cerebral spinal fluid at approximately 1 µM.

The Km values, for L-glutamate, L-aspartate and D-aspartate of the excitatory amino acid carrier protein (EAAC1) and of synaptosomes from cerebellum and striatum are set forth below:

|  | L-Glu | L-Asp | D-Asp |
|---|---|---|---|
| EAAC1 | 12.1 µM | 6.5 µM | 7.5 µM |
| Cerebellum (Ferkaney & Coyle) | 7.6 µM | 7.4 µM | 7.8 µM |
| Striatum (Ferkaney & Coyle) | 10.2 µM | 3.5 µM | 3.8 µM |

Ferkaney, J. & Coyle, J. T., "Heterogeneity of sodium-dependent excitatory amino acid uptake mechanisms in rat brain," *Journal of Neuroscience Research* 16:491–503 (1986).

The pattern of Km values for rabbit derived excitatory amino acid carrier protein is very similar to that of synaptosomes, indicating that the system of the examples reflects the in vivo properties and function of glutamate transport in neurons.

Currents evoked by 50 µM L-glutamate were measured at various potassium ion concentrations. The bath medium were prepared containing potassium ion concentrations in concentrations ranging from 0 mM–50 mM. The bath media were held at a holding potential of −30 mV, and normalized to the current measured on the same oocyte (the value at 0 mM $K^+$ is 100%). Consecutive current measurements were made on single oocytes after changing to bath medium containing the appropriate $K^+$ concentration. After stabilization of membrane current, 50 mM of L-glutamate was applied. The bath medium contained z mM KCl (where z=0–50), 50-z mM choline Cl, 50 mM NaCl, 1.8 mM $CaCl_2$, 1.0 mM $MgCl_2$, 10 mM $BaCl_2$, 5 mM HEPES pH 7.4.

Figure 10:
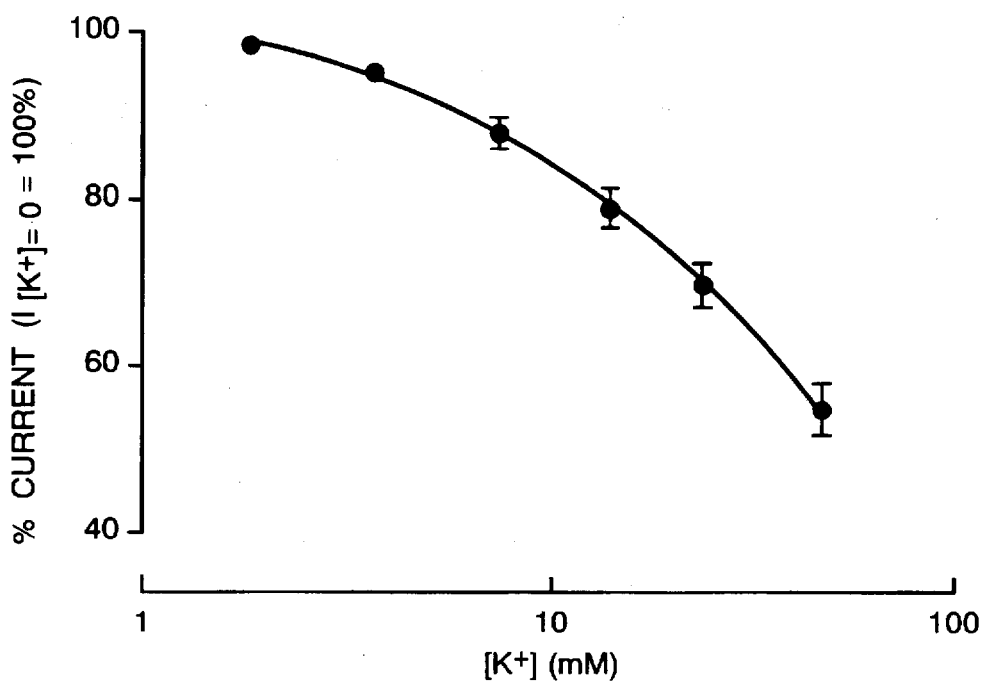
FIG. 10 is a graphical depiction of electrical activity of Xenopus laevis oocytes having an exogenous nucleic acid for the excitatory amino acid carrier protein, at different potassium concentrations.

The results are graphically represented in FIG. 10. Each point represents means±s.e.m. from 6 oocytes. Abscissa indicates external $K^+$ concentration on a logarithmic scale. The data suggests a greater degree of inhibition of current at higher $K^+$ concentration.

EXAMPLE 7

Example 7 illustrates the application of the electrophysiological features of the excitatory amino acid carrier protein, derived from rabbit, described in Example 6 in the screening of drugs to enhance or inhibit the protein. The *Xenopus laevis* oocytes was injected with rabbit derived excitatory amino acid carrier cRNA and processed as described in Example 6. The pharmacologic properties of rabbit derived excitatory amino acid carrier mediated transport were evaluated using inhibitors of L-glutamate uptake previously characterized in studies with synaptosomes. DL-threo-β-hydroxyaspartate (THA) has been reported to be a strong inhibitor of synaptosomal L-glutamate uptake. Robinson, M. B., Hunter-Ensor, M. & Sinor, J., "Pharmacologically distinct sodium-dependent L-[3H]glutamate transport process in rat brain," *Brain Research* 544:196–202 (1991).

The presence of DL-threo-β-hydroxyaspartate inhibited the current evoked by 20 µM L-glutamate. The concentration of the drug which produces 50% inhibition $IC_{50}$ is 7.1 µM. L-α-aminoadipate (AAD) and dihydrokinate (DHK) which are known to be a less effective inhibitors of synaptosomal glutamate transport inhibited glutamate induced inward currents with $IC_{50}$ of 165 µM and >1 mM, respectively, consistent with the experiments using synaptosomes.

This indicates that the expressed excitatory amino acid carrier protein in oocytes exhibits the in vivo pharmacological properties of glutamate transport in neurons. The same method can be applied to the screening of drugs which inhibit or enhance the human glutamate transporter. This method would use *Xenopus laevis* oocytes which express human excitatory amino acid carrier proteins.

EXAMPLE 8

In a number of pathological conditions such as ischemia and anoxia, the extracellular potassium ion concentration is elevated. The elevated extracellular potassium ion concentration may cause reversed transport of glutamate by the high affinity glutamate transporters. The increase in extracellular glutamate concentration leads to neuronal death.

Example 8 demonstrates reversed glutamate transport in excitatory amino acid carrier cRNA-injected oocytes. The method described in this example can be used to screen for drugs which selectively inhibit the reversed glutamate transport (but not glutamate uptake). The drugs can be used clinically for the treatment of pathologic conditions such as brain ischemia after a stroke or anoxia (e.g., during epilepsy or after perinatal asphyxia).

In the case of stroke such drugs could be administered intravenously using continuous drip infusion immediately after the stroke.

The method of this Example can be applied to the screening of drugs which inhibit the reversed glutamate transport of the human excitatory amino acid carrier proteins. This method would use *Xenopus laevis* oocytes which express the human excitatory amino acid carrier protein.

*Xenopus laevis* oocytes were injected with excitatory amino acid carrier cRNA derived from rabbit (25 ng/oocyte) and used for two microelectrode voltage clamp experiments. Recordings were performed at −60 mV in regular ND 96 saline (96 mM NaCl, 2 mM KCl, 1.8 mM $CaCl_2$, 1.0 mM $MgCl_2$ and 5 mM Hepes pH 7.4).

Turning now to FIG. 11, 100 µM L-glutamate was applied to the oocytes. The period of time in which the oocytes were in the presence of L-glutamate is indicated by a bar labeled GLU. The oocytes were responsive to the addition of L-glutamate as depicted in FIG. 11.

Oocytes were then bathed in a solution designated as Solution A having low $Na^+$, high $K^+$ and high glutamate concentrations. Solution A consisted of 0 mM NaCl, 98 mM KCl, 1.8 mM $CaCl_2$, 1.0 mM $MgCl_2$ L-glutamate 10 mM and 5 mM Hepes pH 7.4. Solution A is designed to block reversed transport (glutamate-trans inhibition). Next, Solution A was changed to a second solution designated Solution B. Solution B had no glutamate, but was otherwise identical to Solution A. The Solution B was changed to a third solution, Solution C. Solution C was identical to Solution A. The membrane current, recorded during the period in which the oocytes were exposed to each solution is depicted in FIG. 12. The membrane current was recorded at +30 µV. The electrical activity during the period in which the oocytes were bathed in Solution B, suggests a reversed transport of glutamate.

The outward currents were recorded at varied holding potentials. FIG. 13 depicts the response of the oocytes at each potential.

EXAMPLE 9

Example 9 illustrates a methodology to identify and isolate nucleic acid corresponding to human excitatory amino acid carrier proteins.

Human excitatory amino acid carrier cDNAs were isolated by screening a human kidney and an intestine cDNA library at low stringency using rabbit excitatory amino acid carrier cDNA as a probe. Among the clones isolated were a 3.5 kb kidney cDNA (K-3) and a 3.7 kb intestine cDNA (I-6). Partial sequencing and *Xenopus oocyte* expression indicated that these clones encode the same glutamate transporter. cDNA sequencing of both strands of the entire K-3 coding region revealed an open reading frame from nucleotides 40 to 1611 which encodes a 524 residue protein as depicted in FIG. 1. Like the rabbit protein, the human protein sequences suggest approximately 10 putative membrane spanning domains.

Clones were isolated from the following two cDNA libraries: 1) human kidney lamda-gt10 cDNA library obtained from Graeme Bell, University of Chicago and 2) a human ileum lamda gt10 cDNA library prepared previously from normal human ileum. Approximately 200,000 clones of each library were screened with a gel-purified $^{32}$p-labeled (T7 QuickPrime, Pharmacia) rabbit excitatory amino acid carrier cDNA fragment from nucleotides 175 (NcoI) to 643 (SMAI) as a probe. Hybridization was performed in 50% formamide at 37° C. Filters were washed at 42° C. in 0.1×SSC/0.1% SDS. The following clones containing ECOR1 inserts were isolated (I=intestinal cDNA library; K=kidney cDNA library): I-2 (3.4 kb), I-4 (3.4 kb), I-6 (3.7 kb), I-16 (2.5 kb), K-1 (2b), K-2 (2.8 kb), I-3 (3.5 kb), K-5 (3.5 kb, K-5 (3.8 kt), K-7 (2.8 kb), K-16 (3.3 kb), K-18 (2.8 kb), K-20 (2.8 kb). EcoR1 inserts of clones I-6, K-3 and K-7 were gel-purified, subcloned into pB1 script II SK and used for further analysis. 5'-end cDNA sequencing revealed identical sequences for I-6, K-3 and K-7 except that the length of the 5' non-translated sequences were different (65 nucleotides for clone I-639 for K-3, 8 for K-7). At the 3'-ends only I-6 and K-3 had poly(A) tails. The 3'-untranslated region of I-6 and K-3 is identical except that K-3 is approximately 150 nucleotides shorter than I-6 at the 3'-end. In contrast, the K-7 3'-sequence was unrelated to that of I-6 and K-3 and thus may represent a cloning artifact. *Xenopus laevis* oocyte expression revealed that all three clones stimulated the uptake of $^{14}$C-L-glutamate (50 µM, 1h uptake). The highest stimulation was obtained for clone K-3 (HEAAC1). Using the double stranded sequencing method (Sequenase, USA, OH) both strands of the K-3 cDNA were sequenced. Oligonucleotides were synthesized for use as internal sequencing primers.

EXAMPLE 10

Example 10 describes altering the uptake of L-glutamate in neurons, using anti-sense nucleic acid.

A nucleic acid having eight or more nucleotides is capable of binding to mRNA encoding the excitatory amino acid carrier protein is synthesized. Preferably, the anti-sense nucleic acid has 30 or more nucleotides to provide stability of the hybridization product. The anti-sense nucleic acid can be placed into neurons by microinjection, electroporating calcium chloride or other means.

Anti-sense nucleic acid can be loaded into liposomes for uptake by neurons, as exemplified by U.S. Pat. No. 4,241,046 issued Dec. 23, 1980 to Papahadjopoulos et al.

EXAMPLE 11

A number of references have reported methods of making oligonucleotide analogs and derivatives and their use as anti-sense agents. Examples of references and papers include PCT Application No. PCT/US88/01024, International Publication No. WO88/07544; and PCT Application No. PCT/US91/01010, international Publication No. WO91/16331.

Example 11 features sulfurized oligonucleotide analogs for use as anti-sense agents in accordance with the teachings of International Application No. PCT/US91/01010. A 23 base phosphorothioate oligonucleotide corresponding to the anti-sense of Sequences 177–200 of Seq. ID No. 3 is synthesized by the phosphoramidite method on an automated synthesizer (model 380B Applied Biosystems, Foster City. Calif.). The standard synthesis protocol is followed, except that in the place of the oxidation step, a sulfurization step is substituted, which sulfurization step precedes the capping step. Thus, the synthesis consists of repeated cycles of detritylation, coupling, sulfurization, and capping. Separation of the final product from the synthesis column and purification is accomplished by standard means.

The sulfurization step is performed by exposing the growing chain to a 0.2M solution of 0,0-diisopropylphosphorodithioic acid disulfide in pyridine for one minute at room temperature. The yield of tritylation released during the detritylation steps is anticipated to average 99%. The trityl yield is both a measure of coupling efficiency and a measure of the sulfurization, since nonsulfurized or oxidized trivalent phosophorous linkages in the oligonucleotide are labile to cleavage during detritylation.

The 23 mer corresponding to the anti-sense of Sequences 177–200 of Seq. ID No. 3, after synthesis, is cleaved from the support and deprotected with concentrated ammonium hydroxide at 55° C. for 6 hours. The tritylated oligonucleotide is isolated by HPLC, detritylated, and precipitated as sodium salt. The phosphorothioate analog is resistant to nucleases normally present in cells.

It is anticipated that the 23 mer oligonucleotide analog complementary to Sequences 177–200 of the sense RNA, decreases the translation of mRNA encoding the excitatory amino acid carrier protein.

EXAMPLE 12

Example 12 describes altering the uptake of L-glutamate in neurons.

Nucleic acid corresponding to excitatory amino acid carrier protein is synthesized and coupled to a promoter. The nucleic acid is placed in the neuron by microinjection, electroporating calcium chloride, incorporated into a suitable vector such as a virus, or other means. The neuron is transfected with the nucleic acid carrying the excitatory amino acid carrier protein encoding nucleic acid, or the excitatory amino acid carrier protein nucleic acid is placed in the neuron to transform the neuron to express the protein.

EXAMPLE 13

Example 13 illustrates a method of identifying enhancers and inhibitors of the excitatory amino acid carrier protein. *Xenopus laevis* oocytes are microinjected with cRNA corresponding to the excitatory amino acid carrier protein of Seq. ID No. 1 or 3 using the methodology set forth in Example 1.

Electrophysical measurements are made 3–4 days after injection using a conventional two microelectrode voltage clamp (Axo clamp-2A Axon Instruments, CA) as described in Example 6. The oocytes are maintained in a standard bath solution, containing 96 mM NaCl, 2 mM KCl, 18 mM CaCl$_2$, 1.0 mM MgCl$_2$ and 5 mM HEPES pH 7.4 or in the solutions required to measure the reverse transport (see Example 6b).

Chemicals are added to the standard bath. In the event the cells exhibit a change in current in the presence of the chemical, the chemical may be an enhancer or an inhibitor of excitatory amino acid carrier.

Pharmaceutical articles of manufacture, within the scope of the present invention, include articles wherein the active ingredients thereof are contained in an effective amount to achieve its intended purpose. Determination of the most effective amounts for treatment of each disease associated with defects of the excitatory amino acid carrier protein is within the skill of the art.

In addition to the nucleic acids and proteins of the present invention, pharmaceutical preparations may contain suitable excipients and auxiliaries which facilitate processing of the active compounds. Preferably, the preparations, particularly those which can be administered orally and which can be used for the preferred type of administration, such as tablets, dragees, and capsules, and preparations which can be administered rectally, such as suppositories, as well as suitable solutions for administration parenterally or orally, and compositions which may be administered bucally or sublingually, may contain from 0.1 to 99% by weight of active ingredients, together with the excipient.

EXAMPLE 14

Example 14 illustrates the precise chromosome assignment of the human excitatory amino acid carrier protein. Example 14 also suggests a cause for dicarboxylic aminoaciduria.

A human kidney full-length excitatory amino acid carrier cDNA coding a functional high affinity glutamate transporter (HEAAC1) was isolated from a human kidney cDNA library using the rabbit intestinal excitatory amino acid carrier cDNA as a probe as described in Example 9. The deduced amino acid sequence of human EAAC1 has 92% identity to that of rabbit EAAC1. This human excitatory amino acid carrier cDNA was used as a probe for Southern blot analysis of EcoRI digested DNA from a panel of human/rodent somatic cell hybrids (NIGMS human/rodent somatic cell hybrid mapping panel #1, Coriell Cell Repositories, Camden, N.J.), DNA 10 µg/lane) was digested with EcoRI (Gibco BRL, Gaithersburg, Md.) and separated by 0.8% agarose gel electrophoresis.

Southern analysis of the EcoRI-digested DNA gave bands at 6.5, 5.6, 5.1 and 1.2 kb for human genomic DNA; 7.5 kb for mouse genomic DNA and 7.3, 3.2 and 1 kb for hamster genomic DNA. All four human excitatory amino acid carrier specific bands were observed in the lane corresponding to the human/Chinese hamster hybrid containing chromosome 9 but not in lanes corresponding to any other hybird. Because the human/Chinese hamster hybrid is the only one retaining chromosome 9 this result unambiguously assigns human excitatory amino acid carrier to chromosome 9.

For precise chromosome assignment of the human excitatory amino acid carrier gene we employed FISH. Seven different genomic clones were isolated by screening a human EMBL3 genomic DNA library (Stratagene, La Jolla, Calif.) with $^{32}$P-labelled human kidney excitatory amino acid carrier cDNA probe. Partial sequencing of a PstI fragment (0.7 kb) of a 17 kb genomic clone, which hybridized to the excitatory amino acid carrier cDNA, revealed the presence of an exon coding part of the non-conserved hydrophilic extracellular domain of excitatory amino acid carrier corresponding to residues 163 and 194 in rabbit excitatory amino acid carrier. For FISH analysis, the 17 kb insert of this genomic clone was gel purified from a 0.6% agarose gel using Geneclean II (method as described by the manufacturers for high molecular weight DNAs, Biolab 101 Inc. La Jolla, Calif.). Purified insert was labeled with biotin-11-dUTP using a BioNick labeling system (Gibco BRL). Hybridization was performed with the EAAC1 probe at a concentration of 2.5 µg/ml. Thirty-seven methaphases were assessed for probe localization. Map position of the EAAC1 probe was assigned by visual inspection of the fluorescent signal on the DAPI-stained metaphase chromosomes. The human EAAC1 gene was assigned to 9p24.

A mutation in the human excitatory amino acid carrier gene is a likely explanation for the cause of dicarboxylic aminoaciduria with accompanying neurological abnormalities. The human excitatory amino acid carrier protein is strongly expressed in human kidney and brain and the characteristics of this disorder are consistent with dysfunction of such carrier protein in these tissues.

One form of familial ALS has been linked to chromosome 21 at the location of the SOD1 gene. A mutation in the human excitatory amino acid carrier gene, however, may be associated with other forms of familial ALS.

EXAMPLE 15

This example highlights an assessment of the role of the human derived excitatory amino acid carrier protein in synaptic transmission. Modulation of the function of neuronal high affinity glutamate transport at pre-synaptic terminals may be crucial during the transmission process. These data suggest that L-trans-pyrolidine-2, 4-dicarboxylate (PDC) is the preferred uptake inhibitor. In contrast, D-L-theo-B-hydroxyaspartate (THA) and α-aminoadipate (AAD), PDC reduces the maximal transport rate (Vmax) of glutamate uptake. An inherent disadvantage of all these inhibitors is that they are transport substrates of the human excitatory amino acid carrier protein.

The ability of the glutamate uptake inhibitor PDC, THA, AAD and dihydrokainate (DHK) to inhibit the currents evoked in *Xenopus laevis* oocytes by L-glutamate at different L-glutamate concentrations was studied. Concentrations of 10, 50, 100 µM L-glutamate were evaluated for THA, AAD, DHK and concentrations of 100 and 1000 µM L-glutamate were evaluated for PDC. The inhibitor concentrations used were 5, 25, 50, 100 and 300 µM (THA or AAD) and 10, 50, 100, 300 and 600 µM for PDC and 1 mM for DHK. The glutamate evoked currents were first measured without addition of inhibitor. Subsequent measurements were performed at constant inhibitor concentrations with progressive increase of the L-glutamate concentration with intermittent washes of inhibitor solution alone. The glutamate evoked current without inhibitor at the end of each series of inhibition experiments was −30% reduced compared to the initial amplitude and recovered only partially after a 60 minute incubation of oocytes. This may be due to intracellular accumulation of glutamate and inhibitor resulting in trans-stimulation or trans-inhibition. The initial L-glutamate-evoked currents were used for the calculation of the $IC_{50}$ values. Calculation of $K_I$ values was based on the kinetics for competitive inhibition. These results are summarized in Table 1 below:

TABLE I

Characteristics of the Human High Affinity Glutamate Transporter HEAAC1

|  | $K_m$ (µM) | $K_i$ (µM) | $IC_{50}$ L-Glu = 100 um | $IC_{50}$ L-Glu = 1 mM |
|---|---|---|---|---|
| L-glutamate (L-GLU) | 30 ± 3.0 | — | — | — |
| D,L-threo-β-hydroxyaspartate (THA) | 34 ± 6.4 | n.d. | 28 ± 0.8 | n.d. |
| L-trans-pyrolidine-2,4-dicarboxyiate (PDC) | 23 ± 3.7 | ~1. g | 74 ± 11 | 91 ± 7.2 |
| L α-aminoadipatate (AAD) | 2400 ± 0.6 | ~20 | n.d. | n.d. |
| Dihydrokainate (DHK) | >1 mM | n.d. | 6.7% inhibition at 1 mM DHK | |

All known inhibitors of brain glutamate uptake which were tested are either substrates of the human excitatory amino acid carrier protein or have no significant effect on transport. Threo-β-hydroxyaspartate and L-trans 2, 4,-dicarboxylic acid (PDC) induced large inward currents, whereas L-α-aminoadipate (AAD) induced a small current at 50 μM. Dihydrokainate (DHK) did not induce significant currents even when used at concentrations of up to 1 mM. The $K_m$ values for THA and PDC as shown in Table 1 were similar to that of L-glutamate. THA and PDC were potent inhibitors of the current induced by L-glutamate at 10–1,000 μM. DHK, however, did not inhibit the current efficiently, even when used at high concentrations (1 mM). The order of sensitivity to these inhibitors based on $IC_{50}$ values (50% inhibition of the current induced by 100 μM L-glutamate) is THA>PDC>>AAA>DHK. This order parallels that of decreasing $K_m$ values for these substrates, indicating that the inhibitors act as transport substrates and inhibit L-glutamate uptake by competitive inhibition.

EXAMPLE 16

This Example highlights steady-state and pre-steady-state currents mediated by human derived excitatory amino acid carrier protein.

Oocytes were used for two-microelectrode voltage-clamping as described above and command potentials were applied and controlled by an IBM-compatible computer via the software CLAMPEX from pCLAMP (version 5.5 Axon Instruments, CA). The oocyte membrane was held at −50 mV and pulsed to the test potential for msec followed by a 1 sec interpulse interval at the holding potential of −50 mV before application of the next pulse. Current was low-pass filtered at 50 kHz, digitized at 200 μsec and saver on the computer. Steady-state currents were obtained by averaging the current between 72 and 76 msec.

The $K_m$ for L-glutamate strongly depended on membrane voltage suggesting that glutamate binding (or a closely related step) occurs within the membrane-spanning portion of the human excitatory amino acid carrier. Thus, in order for the negatively charged glutamate ion to reach its binding site it has to move against the electrical potential. This is consistent with the observation that hyperpolarization decreases the affinity for glutamate. Positively charged residues located within the membrane electric field such as Lys 228, Lys 269, His 260 and His 296 may facilitate glutamate binding by neutralizing its negative charge.

The data suggest that the electrogenic properties displayed by the human excitatory amino acid carrier are distinct from those of SGLT1 and GAT-1 and indicate that the voltage-dependent and rate-limiting steps of transport are different among these transporters. In SGLT1, the relocation of the empty carrier as well as $Na^+$-binding/dissociation are voltage-dependent and the former is the rate limiting step of transport. In GAT-1, $Na^+$-binding (or a closely related step) is voltage-dependent, whereas the rate-limiting step of transport is predicted to be voltage-independent. In the human excitatory amino acid carrier, in contrast, glutamate-binding (or a closely related step) is voltage dependent. Studies of the rabbit kidney high affinity glutamate transporter revealed that the charge-translocating step (movement of $2Na^+$ and one glutamate molecule across the membrane) is rate-limiting. The findings on the human excitatory amino acid carrier are consistent with this hypothesis because the current evoked at high glutamate concentrations did not saturate with hyperpolarization down to −150 mV and because the Vmax increased with hyperpolarization. The observation that the current evoked by low glutamate concentrations saturated with membrane hyperpolarization, however, strongly suggests that at glutamate concentrations near or below the $K_m$ value the glutamate-binding becomes rate limiting. Since the affinity for glutamate decreases with hyperpolarization a glutamate concentration of 10 μM will be substantially below its $K_m$ value at membrane potentials below −60 mV.

In SGLT1, which has a predicted valency of −2, the relocation step of the empty carrier is electrogenic (the valency herein refers to all movable charges on the carrier within the membrane electric field). In contrast to SGLT1, the relocation step of the glutamate transporter is predicted to be an electroneutral process. The valency of the empty excitatory human amino acid carrier may be zero and that binding the $K^+$ and OH to the inside of the empty carrier serves to accelerate the relocation step in an electroneutral manner to such an extent that its rate exceeds that of the charge-translocating step (i.e. the step in which the substrates are translocated across the membrane).

Although the Vmax for the PDC-induced current is markedly reduced, the overall voltage-dependencies for the L-glutamate and PDC evoked currents are identical. This suggests that the excitatory amino acid carrier-PDC complex and the excitatory amino acid carrier-glutamate complex behave similarly within the membrane electric field. A possible explanation for the reduced Vmax of PDC is that the turnover rate for PDC is reduced, e.g. due to slower translocation and/or slower dissociation of PDC. The similar voltage dependences of Vmax for both L-glutamate and PDC, suggests that PDC slows down the rate limiting charge translocation step. This interpretation is reasonable considering the relatively rigid molecular structure of PDC compared with L-glutamate (Bridges, 1991 #319). In contrast to SGLT1 and GAT-1, human excitatory amino acid carrier exhibited no detectable pre-steady state currents in the presence of $Na^+$ and the absence of glutamate. For SGLT1, pre-steady-state currents in the presence of $Na^+$ and in the absence of glucose are predicted to be the result of the movement of the negatively charged empty carrier within the membrane electric field subsequent to the dissociation of $Na^+$. Relocation of the negatively charged empty carrier was modeled to be the rate-limiting step for SGLT1-mediated transport. In contrast, the lack of current relaxation for the human excitatory amino acid carrier in the presence of $Na^+$ and in the absence of glutamate is consistent with the model that the human excitatory amino acid carrier is electroneutral within the membrane electric field.

The minor relaxation currents of the human excitatory amino acid carrier for depolarizing pulses in the presence of $Na^+$ and glutamate could be explained by the movement of glutamate as part of the $2Na^+$-glutamate-carrier complex within the membrane electric field. Because the charge translocation process is modeled to be rate-limiting, the majority of the transporters in the membrane are predicted to exist in this form. The potential-dependence of the $K_m$ L-glutamate predicts that the glutamate binding site is buried in the membrane and that depolarizing pulses result in a significant increase in the affinity for glutamate. Thus, depolarizing voltage jumps may result in tighter substrate binding and this may be associated with a slight inward movement of glutamate resulting in an outwardly directed relaxation current.

EXAMPLE 17

Pharmaceutical articles of the present invention are manufactured in a way which is itself well known in the art. For example, the pharmaceutical preparations may be made by means of conventional mixing, granulating, dragee-making, dissolving, or lyophilizing processes. The process to be used will depend ultimately on the physical properties of the active ingredient used.

Suitable excipients are, in particular, fillers such as sugars, for example, lactose or sucrose, mannitol or sorbitol, cellulose preparations and/or calcium, phosphates, or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate, and/or polyethylene glycol. Dragee cores may be provided with suitable coating which, if desired, may be resistant to gastric juices. For this purpose, concentrated sugar solutions may be used, which may optionally contain gum arabic, talc, polyvinylpyrrolidone, polyethylene glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs and pigments may be added to the tablets of dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyloleate or triglycerides. Aqueous injection suspensions may contain substances which increase the viscosity of the suspension, for example, sodium carboxymethyl cellulose, sorbitol, and/or dextran. Optionally, the suspension may also contain stabilizers.

Additionally, the compounds of the present invention may also be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as dicetylphosphate, stearylamine, or phosphatidic acid, and/or other materials of a hydrophobic nature. The diameters of the liposomes generally range from about 15 nm to 5 microns.

Thus, while preferred embodiments of the present invention have been described, the present invention is capable of variation and modification and, therefore, the invention should not be limited to the precise details set forth, but should include such changes and alterations that fall within the purview of the following claims.

We claim:

1. An isolated excitatory amino-acid carrier protein having an amino acid sequence corresponding to a sequence within Seq. ID No. 1.

2. An isolated excitatory amino-acid carrier protein having an amino acid sequence corresponding to a sequence within Seq. ID No. 3.

3. An isolated excitatory amino-acid carrier protein having an amino acid sequence as set forth in Seq. ID No. 2.

4. An isolated excitatory amino-acid carrier protein having an amino acid sequence as set forth in Seq. ID No. 4.

5. An isolated excitatory amino acid carrier protein exhibiting high affinity for L-glutamate, said protein having an amino acid sequence corresponding to a nucleic acid sequence within Seq. ID No. 1 or Seq. ID No. 3.

6. An isolated amino acid carrier protein encoded by a nucleic acid comprising a sequence of nucleotides selected from the group consisting of nucleotides 40–1611 of Seq I.D. No. 1 and 177–1749 of Seq I.D. No. 3.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1620 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: HOMO SAPIENS ( x i ) SEQUENCE DESCRIPTION: SEQ ID NO:1:

| | | | | | | |
|---|---|---|---|---|---|---|
| GCGCACGGCC | GAGCCCAGCG | CACAATAGCG | GCGACAGCCA | TGGGGAAACC | GGCGAGGAAA | 60 |
| GGATGCGAGT | GGAAGCGCTT | CCTGAAGAAT | AACTGGGTGT | TGCTGTCCAC | CGTGGCCGCG | 120 |
| GTGGTGCTAG | GCATTACCAC | AGGAGTCTTG | GTTCGAGAAC | ACAGCAACCT | CTCAACTCTA | 180 |
| GAGAAATTCT | ACTTTGCTTT | TCCTGGAGAA | ATTCTAATGC | GGATGCTGAA | ACTCATCATT | 240 |
| TTGCCATTAA | TTATATCCAG | CATGATTACA | GGTGTTGCTG | CACTGGATTC | CAACGTATCC | 300 |
| GGAAAAATTG | GTCTGCGCGC | TGTGCTGTAT | TATTTCTGTA | CCACTCTCAT | TGCTGTTATT | 360 |
| CTAGGTATTG | TGCTGGTGGT | GAGCATCAAG | CCTGGTGTCA | CCCAGAAAGT | GGGTGAAATT | 420 |
| GCGAGGACAG | GCAGCACCCC | TGAAGTCAGT | ACGGTGGATG | CCATGTTAGA | TCTCATCAGG | 480 |
| AATATGTTCC | CTGAGAATCT | TGTCCAGGCC | TGTTTTCAGC | AGTACAAAAC | TAAGCGTGAA | 540 |
| GAAGTGAACC | CTGCCAGTGA | TCCAGAGATG | AACATGACAG | AAGAGTCCTT | CACAGCTGTC | 600 |
| ATGACAACTG | CAATTTCCAA | GAACAAAACA | AAGGAATACA | AAATTGTTGG | CATGTATTCA | 660 |
| GATGGCATAA | ACGTCCTGGG | CTTGATTGTC | TTTTGCCTTG | TCTTTGGACT | TGTCATTGGA | 720 |
| AAAATGGGAG | AAAAGGGACA | AATTCTGGTG | GATTTCTTCA | ATGCTTTGAG | TGATGCAACC | 780 |
| ATGAAAATCG | TTCAGATCAT | CATGTGTTAT | ATGCCACATG | GTATTTGTT | CCTGATTGCT | 840 |
| GGGAAGATCA | TAGAAGTTGA | AGACTGGGAA | ATATTCCGCA | AGCTGGGCCT | TTACATGGCC | 900 |
| ACAGTCCTGA | CTGGGCTTGC | AATCCACTCC | ATTGTAATTC | TCCCGCTGAT | ATATTTCATA | 960 |
| GTCGTACGAA | AGAACCCTTT | CCGATTTGCC | ATGGGAATGG | CCCAGGCTCT | CCTGACAGCT | 1020 |
| CTCATGATCT | CTTCCAGTTC | AGCAACACTG | CCTGTCACCT | TCCGCTGTGC | TGAAGAAAAT | 1080 |
| AACCAGGTGG | ACAAGAGGAT | CACTCGATTC | GTGTTACCCG | TTGGTGCAAC | AATCAACATG | 1140 |
| GATGGGACTG | CGCTCTATGA | AGCAGTGGCA | GCGGTGTTTA | TTGCACAGTT | GAATGACCTG | 1200 |
| GACTTGGGCA | TTGGGCAGAT | CATCACCATC | AGTATCACGG | CCACATCTGC | CAGCATCGGA | 1260 |
| GCTGCTGGCG | TGCCCCAGGC | TGGCCTGGTG | ACCATGGTGA | TTGTGCTGAG | TGCCGTGGGC | 1320 |
| CTGCCCGCCG | AGGATGTCAC | CCTGATCATT | GCTGTCGACT | GGCTCCTGGA | CCGGTTCAGG | 1380 |
| ACCATGGTCA | ACGTCCTTGG | TGATGCTTTT | GGGACGGGCA | TTGTGGAAAA | GCTCTCCAAG | 1440 |
| AAGGAGCTGG | AGCAGATGGA | TGTTTCATCT | GAAGTCAACA | TTGTGAATCC | CTTTGCCTTG | 1500 |
| GAATCCACAA | TCCTTGACAA | CGAAGACTCA | GACACCAAGA | AGTCTTATGT | CAATGGAGGC | 1560 |
| TTTGCAGTAG | ACAAGTCTGA | CACCATCTCA | TTCACCCAGA | CCTCACAGTT | CTAGGGCCCT | 1620 |

( 2 ) INFORMATION FOR SEQ ID NO:2:

( i ) SEQUENCE CHARACTERISTICS:
        ( A ) LENGTH: 524 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: HOMO SAPIENS ( x i ) SEQUENCE DESCRIPTION: SEQ ID NO:2:

Met  Gly  Lys  Pro  Ala  Arg  Lys  Gly  Cys  Glu  Trp  Lys  Arg  Phe  Leu  Lys
    1                5                    10                  15

Asn  Asn  Trp  Val  Leu  Leu  Ser  Thr  Val  Ala  Ala  Val  Val  Leu  Gly  Ile

-continued

```
                          20                          25                          30
Thr  Thr  Gly  Val  Leu  Val  Arg  Glu  His  Ser  Asn  Leu  Ser  Thr  Leu  Glu
          35                      40                     45
Lys  Phe  Tyr  Phe  Ala  Phe  Pro  Gly  Glu  Ile  Leu  Met  Arg  Met  Leu  Lys
     50                      55                      60
Leu  Ile  Ile  Leu  Pro  Leu  Ile  Ile  Ser  Ser  Met  Ile  Thr  Gly  Val  Ala
65                       70                      75                          80
Ala  Leu  Asp  Ser  Asn  Val  Ser  Gly  Lys  Ile  Gly  Leu  Arg  Ala  Val  Leu
               85                      90                          95
Tyr  Tyr  Phe  Cys  Thr  Thr  Leu  Ile  Ala  Val  Ile  Leu  Gly  Ile  Val  Leu
               100                     105                     110
Val  Val  Ser  Ile  Lys  Pro  Gly  Val  Thr  Gln  Lys  Val  Gly  Glu  Ile  Ala
          115                     120                     125
Arg  Thr  Gly  Ser  Thr  Pro  Glu  Val  Ser  Thr  Val  Asp  Ala  Met  Leu  Asp
     130                     135                     140
Leu  Ile  Arg  Asn  Met  Phe  Pro  Glu  Asn  Leu  Val  Gln  Ala  Cys  Phe  Gln
145                     150                     155                          160
Gln  Tyr  Lys  Thr  Lys  Arg  Glu  Glu  Val  Asn  Pro  Ala  Ser  Asp  Pro  Glu
               165                     170                     175
Met  Asn  Met  Thr  Glu  Glu  Ser  Phe  Thr  Ala  Val  Met  Thr  Thr  Ala  Ile
               180                     185                     190
Ser  Lys  Asn  Lys  Thr  Lys  Glu  Tyr  Lys  Ile  Val  Gly  Met  Tyr  Ser  Asp
          195                     200                     205
Gly  Ile  Asn  Val  Leu  Gly  Leu  Ile  Val  Phe  Cys  Leu  Val  Phe  Gly  Leu
          210                     215                     220
Val  Ile  Gly  Lys  Met  Gly  Glu  Lys  Gly  Gln  Ile  Leu  Val  Asp  Phe  Phe
225                     230                     235                          240
Asn  Ala  Leu  Ser  Asp  Ala  Thr  Met  Lys  Ile  Val  Gln  Ile  Ile  Met  Cys
               245                     250                          255
Tyr  Met  Pro  His  Gly  Ile  Leu  Phe  Leu  Ile  Ala  Gly  Lys  Ile  Ile  Glu
               260                     265                     270
Val  Glu  Asp  Trp  Glu  Ile  Phe  Arg  Lys  Leu  Gly  Leu  Tyr  Met  Ala  Thr
          275                     280                     285
Val  Leu  Thr  Gly  Leu  Ala  Ile  His  Ser  Ile  Val  Ile  Leu  Pro  Leu  Ile
     290                     295                     300
Tyr  Phe  Ile  Val  Val  Arg  Lys  Asn  Pro  Phe  Arg  Phe  Ala  Met  Gly  Met
305                     310                     315                          320
Ala  Gln  Ala  Leu  Leu  Thr  Ala  Leu  Met  Ile  Ser  Ser  Ser  Ala  Thr
                    325                     330                     335
Leu  Pro  Val  Thr  Phe  Arg  Cys  Ala  Glu  Glu  Asn  Asn  Gln  Val  Asp  Lys
               340                     345                     350
Arg  Ile  Thr  Arg  Phe  Val  Leu  Pro  Val  Gly  Ala  Thr  Ile  Asn  Met  Asp
          355                     360                     365
Gly  Thr  Ala  Leu  Tyr  Glu  Ala  Val  Ala  Ala  Val  Phe  Ile  Ala  Gln  Leu
     370                     375                     380
Asn  Asp  Leu  Asp  Leu  Gly  Ile  Gly  Gln  Ile  Ile  Thr  Ile  Ser  Ile  Thr
385                     390                     395                          400
Ala  Thr  Ser  Ala  Ser  Ile  Gly  Ala  Ala  Gly  Val  Pro  Gln  Ala  Gly  Leu
               405                     410                     415
Val  Thr  Met  Val  Ile  Val  Leu  Ser  Ala  Val  Gly  Leu  Pro  Ala  Glu  Asp
               420                     425                     430
Val  Thr  Leu  Ile  Ile  Ala  Val  Asp  Trp  Leu  Leu  Asp  Arg  Phe  Arg  Thr
          435                     440                     445
```

|   |   |   |   |   |   |   |   |   |   |   |   |   |   |   |
|---|---|---|---|---|---|---|---|---|---|---|---|---|---|---|
| Met | Val | Asn | Val | Leu | Gly | Asp | Ala | Phe | Gly | Thr | Gly | Ile | Val | Glu | Lys |
|  | 450 |  |  |  | 455 |  |  |  |  | 460 |  |  |  |  |

```
    Met  Val  Asn  Val  Leu  Gly  Asp  Ala  Phe  Gly  Thr  Gly  Ile  Val  Glu  Lys
         450                 455                      460

Leu  Ser  Lys  Lys  Glu  Leu  Glu  Gln  Met  Asp  Val  Ser  Ser  Glu  Val  Asn
    465                 470                      475                           480

Ile  Val  Asn  Pro  Phe  Ala  Leu  Glu  Ser  Thr  Ile  Leu  Asp  Asn  Glu  Asp
                   485                      490                           495

Ser  Asp  Thr  Lys  Lys  Ser  Tyr  Val  Asn  Gly  Gly  Phe  Ala  Val  Asp  Lys
                   500                      505                      510

Ser  Asp  Thr  Ile  Ser  Phe  Thr  Gln  Thr  Ser  Gln  Phe
                   515                      520
```

( 2 ) INFORMATION FOR SEQ ID NO:3:

( i ) SEQUENCE CHARACTERISTICS:
        ( A ) LENGTH: 3442 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: LEPORIDAE (RABBIT)

( x i ) SEQUENCE DESCRIPTION: SEQ ID NO:3:

```
AGGCGGCGGT GACAGCGGCA TCGGCAGGGC CAGCGCGCAC TCTCTCCCAG GCGCACCGGC    60
GTCTTGCTTC CTCCGCGCCG CCCAGCTGAC GGCCATCCCC GGCCGAGGCG CGCACAGCCC   120
AGCCCCGCAC ACAACAGCGG CGACCGCGGG GCCCGCTCGG AGCCCGGACG CCGCCATGG    180
GGAAGCCGGC GAGGAAAGGA TGCGACAGCA AGCGCTTCCT GAAGAATAAC TGGCTGCTGC   240
TCTCCACCGT GGTCGCGGTG GTGCTAGGCA TTGTCATAGG AGTCTTGGTT CGAGAATACA   300
GCAATCTCTC AACTCTGGAT AAATTCTACT TTGCTTTTCC TGGAGAAATC CTGATGAGGA   360
TGCTGAAACT CGTCATTCTG CCATTAATTG TATCCAGCAT GATTACAGGT GTTGCTGCAC   420
TGGATTCCAA TGTTTCTGGG AAAATTGGTC TGCGTGCTGT CTTGTATTAT TTCTGCACCA   480
CTATCATTGC TGTAATTCTA GGTATTGTGT TGGTGGTGAG CATCAAGCCT GGGGTCACCC   540
AGAAAGTGGA TGAAATCGAC AGGACAGGCA GCACCCCTGA AGTCAGCACA GTGGATGCCA   600
TGTTAGACCT GATCAGGAAT ATGTTCCCTG AGAACCTCGT GCAGGCCTGT TTTCAGCAGT   660
ACAAAACCAC TCGTGAAGAA GTGACAGCTT CCGATGATAC AGGGAAGAAT GGGACTGAAG   720
AGTCTGTCAC AGCCGTCATG ACAACAGCCG TGTCTGAGAA CAGAACAAAG GAGTACAGAG   780
TCGTGGGCCT GTATTCAGAT GGCATCAATG TCCTGGGCTT GATTGTCTTC TGCCTCGTGT   840
TCGGACTCGT CATCGGGAAA ATGGGAGAAA AGGGACAGAT TCTGGTGGAT TTCTTCAATG   900
CTTTGAGTGA CGCAACCATG AAAATCGTTC AGATCATTAT GTGTTACATG CCGCTTGGTA   960
TTTTGTTCCT GATTGCCGGG AAGATCATAG AAGTTGAAGA CTGGGAAATT TTCCGCAAGC  1020
TGGGCTTGTA CATGGTCACC GTCCTGAGTG GGCTTGCAAT CCACTCCATT GTCATTCTCC  1080
CACTGATATA TTTCATTGTG GTGCGAAAGA ACCCTTTCCG ATTTGCCATG GGAATGACCC  1140
AGGCTCTCCT GACAGCACTC ATGATCTCTT CCAGTTCAGC AACACTGCCT GTCACCTTCC  1200
GCTGTGCAGA AGAAAAGAAC CGTGTGGACA AGAGGATCAC TCGATTTGTG TTGCCCGTTG  1260
GTGCCACAAT CAACATGGAT GGGACCGCAC TCTATGAGGC AGTGGCAGCA GTGTTTATTG  1320
CACAGTTGAA TGATATGGAC TTGAGCATTG GGCAGATCAT CACTATCAGC GTCACAGCTA  1380
```

| | | | | | |
|---|---|---|---|---|---|
|CAGCTGCCAG|CATTGGAGCT|GCCGGTGTGC|CCCAGGCTGG|CCTGGTGACC|ATGGTGATTG 1440|
|TGCTGAGTGC|TGTGGGGCTG|CCCGCTGAGG|ATGTCACCCT|GATCATTGCT|GTCGACTGGC 1500|
|TCCTGGACCG|GTTCAGGACT|GTGGTCAACG|TCCTTGGTGA|TGCTTTTGGA|ACCGGCATTG 1560|
|TGGAAAAGCT|CTCCAAGAAG|GAGTTGGAGC|AGATGGATGT|TCATCTGAA|GTCAACATCG 1620|
|TGAACCCTTT|TGCCTTGGAA|TCTGCAACCC|TCGACAACGA|AGACTCAGAC|ACCAAGAAGT 1680|
|CCTACATCAA|CGGAGGATTT|GCAGTAGACA|AGTCTGACAC|AATCTCTTTC|ACCCAGACCT 1740|
|CACAGTTCTA|GAGGCACTGG|CTTCACAGGA|CTGTCATGAA|GGACCTTCCA|TGAGAGTCAT 1800|
|CTCTTAGCAA|ATGCAAACAT|TAATTAAGGA|AAATGCAAAT|GGCCACTGTA|CATTTAATTT 1860|
|GATATACAGA|CCTCCAGATT|ATTTTCTATA|TTCAAATTCT|GAGCCTTTGC|TCTCTGGGTT 1920|
|TTGGGATTTG|GGGCAGGGTG|GGGTAACATG|AAAGGAAATT|CTTGAAAGTT|GTATTATCTG 1980|
|AATTTTTTAA|AATTCCATAG|GCCAAAGTTT|AGAAGTATGC|AAACTAACTT|GGAATTAGAT 2040|
|AATGGGTATG|GAAGAGAAAT|TGCTTTTTCA|TGTACAGACT|AGTATTTTTT|AAAAAATAAT 2100|
|TCTGTCATTG|GTTACAAATT|TTTACTCAGG|CTTTCTATTG|GCATGGATTT|CCTTTGACCT 2160|
|CACTTTTTTA|TAGATTATTC|TTCATCTAAC|CTTCCCCACT|AATGTGCCAA|ATTGTCCATA 2220|
|CTGAACTCCT|TTCTAGCCAA|TTTCAAAGAA|ATTGCTTTGA|AAGAAAACAA|ACCAGCACAG 2280|
|TTCCTCAATA|ACAGTCTTAA|GATGGGTATA|GGCTTTGGGG|AGGGAAGGAG|ACGAGTTCTT 2340|
|TTACTAATGT|ACTGTATTGG|GATGCTGATA|ACTGTTAACC|CAGTGTTCAC|TATAGAGCTA 2400|
|TATATATATA|TATGTATGTA|TGTGTATGTA|TATATTTATT|ATTTTCATAT|AATTCGCCAG 2460|
|AGATCAGAAT|TGAACTGTCA|ATGTGAAATA|AAGAGCTGTC|CTTGTACTTG|AATAGTTATT 2520|
|ACAATTCCAA|CCCAGATCTG|CTGTGGGGCT|TATCAGAACT|CTTTTCCTTT|TTATCAGAAT 2580|
|TAGAGAAATC|ATGTTGTCGG|ATCACTTAAG|GTCTGTGTAT|CAGCCCCAAG|CAGAGATGTA 2640|
|TTGTGGTGAC|AGTCCAGGCT|GGCCATTCAC|TTACATCTCC|CAGATTGGTG|CTGCCTGGAG 2700|
|TGAACCCATA|TCAGCTGTAC|ATAAGACTGC|ACACAAAGGT|GCCACTCATG|AAAGGCTGGA 2760|
|CGTGCTTTTA|TCTAATTAGA|AGGCCTCCTT|CTCCTGTGTG|GACTCATGCC|AGGTAGAGAA 2820|
|ACATTTGCT|GGCCTTGCAC|TTTTGTATCC|ATCAGCACCC|AAACAACAGT|GGCAGATGAC 2880|
|CAGCTACGTT|GCATTTGAAT|ATAGAATCCA|CGGTTTGAAC|AAGCCACACT|GCAGAAAAAG 2940|
|AGCTGTGTCA|ACCCTGGGTT|CTTGCAGAGT|AAACCACGGG|ACCTGAGACG|CTGGTGCCAG 3000|
|CAGGTGAGGA|GTGAGTCTTC|CATTCTGCAA|CGCTTGTCTC|CTCCTCTAAC|GATGGCTTCA 3060|
|CTGTTAATCT|TGGCCCTGTT|CATTAAAATC|CTTTGCTTGT|CATCCTCCTG|CTAATTTATG 3120|
|AAGATAACTG|ATAAAAGTCT|GTGCTTCAGT|TCTCATCTTG|TAAATAATGC|TTAACATGTA 3180|
|CTTACACTGG|CATCCAAAAC|AGTAATGCAG|TCTTATGTAG|CCAGCTCAAA|CATGTGCTTT 3240|
|TAAAATTAAG|CCAGAAATTG|TGCCAAAGAA|AGCAGGGAAG|TAAATACTCA|GTATTGACCA 3300|
|TCTGCAGCTG|AAACTATGAG|ACTGATACCG|AACCGTCATG|TAATCATCAT|AGTAACCAGT 3360|
|GGTTCAATGT|GAATTTTAAA|ATGGAATTAT|TGGTATTGTT|ATAGGAAATA|AATAGAGCTG 3420|
|TAAATGAAAA|AAAAAAAAAA|AA| | | 3442|

( 2 ) INFORMATION FOR SEQ ID NO:4:

( i ) SEQUENCE CHARACTERISTICS:
        ( A ) LENGTH: 524 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
    ( A ) ORGANISM: LEPORIDAE (RABBIT)

( x i ) SEQUENCE DESCRIPTION: SEQ ID NO:4:

```
Met Gly Lys Pro Ala Arg Lys Gly Cys Asp Ser Lys Arg Phe Leu Lys
 1               5                  10                  15

Asn Asn Trp Leu Leu Leu Ser Thr Val Val Ala Val Val Leu Gly Ile
            20                  25                  30

Val Ile Gly Val Leu Val Arg Glu Tyr Ser Asn Leu Ser Thr Leu Asp
        35                  40                  45

Lys Phe Tyr Phe Ala Phe Pro Gly Glu Ile Leu Met Arg Met Leu Lys
    50                  55                  60

Leu Val Ile Leu Pro Leu Ile Val Ser Ser Met Ile Thr Gly Val Ala
65                  70                  75                  80

Ala Leu Asp Ser Asn Val Ser Gly Lys Ile Gly Leu Arg Ala Val Leu
                85                  90                  95

Tyr Tyr Phe Cys Thr Thr Ile Ile Ala Val Ile Leu Gly Ile Val Leu
            100                 105                 110

Val Val Ser Ile Lys Pro Gly Val Thr Gln Lys Val Asp Glu Ile Asp
        115                 120                 125

Arg Thr Gly Ser Thr Pro Glu Val Ser Thr Val Asp Ala Met Leu Asp
    130                 135                 140

Leu Ile Arg Asn Met Phe Pro Glu Asn Leu Val Gln Ala Cys Phe Gln
145                 150                 155                 160

Gln Tyr Lys Thr Thr Arg Glu Glu Val Thr Ala Ser Asp Asp Thr Gly
                165                 170                 175

Lys Asn Gly Thr Glu Glu Ser Val Thr Ala Val Met Thr Thr Ala Val
            180                 185                 190

Ser Glu Asn Arg Thr Lys Glu Tyr Arg Val Val Gly Leu Tyr Ser Asp
        195                 200                 205

Gly Ile Asn Val Leu Gly Leu Ile Val Phe Cys Leu Val Phe Gly Leu
    210                 215                 220

Val Ile Gly Lys Met Gly Glu Lys Gly Gln Ile Leu Val Asp Phe Phe
225                 230                 235                 240

Asn Ala Leu Ser Asp Ala Thr Met Lys Ile Val Gln Ile Ile Met Cys
                245                 250                 255

Tyr Met Pro Leu Gly Ile Leu Phe Leu Ile Ala Gly Lys Ile Ile Glu
            260                 265                 270

Val Glu Asp Trp Glu Ile Phe Arg Lys Leu Gly Leu Tyr Met Val Thr
        275                 280                 285

Val Leu Ser Gly Leu Ala Ile His Ser Ile Val Ile Leu Pro Leu Ile
    290                 295                 300

Tyr Phe Ile Val Val Arg Lys Asn Pro Phe Arg Phe Ala Met Gly Met
305                 310                 315                 320

Thr Gln Ala Leu Leu Thr Ala Leu Met Ile Ser Ser Ser Ala Thr
                325                 330                 335

Leu Pro Val Thr Phe Arg Cys Ala Glu Glu Lys Asn Arg Val Asp Lys
            340                 345                 350

Arg Ile Thr Arg Phe Val Leu Pro Val Gly Ala Thr Ile Asn Met Asp
        355                 360                 365
```

| | | | | | | | | | | | | | | |
|---|---|---|---|---|---|---|---|---|---|---|---|---|---|---|
| Gly | Thr 370 | Ala | Leu | Tyr | Glu | Ala 375 | Val | Ala | Ala | Val | Phe 380 | Ile | Ala | Gln | Leu |
| Asn 385 | Asp | Met | Asp | Leu | Ser 390 | Ile | Gly | Gln | Ile | Ile 395 | Thr | Ile | Ser | Val | Thr 400 |
| Ala | Thr | Ala | Ala | Ser 405 | Ile | Gly | Ala | Ala | Gly 410 | Val | Pro | Gln | Ala | Gly 415 | Leu |
| Val | Thr | Met | Val 420 | Ile | Val | Leu | Ser | Ala 425 | Val | Gly | Leu | Pro | Ala 430 | Glu | Asp |
| Val | Thr | Leu 435 | Ile | Ile | Ala | Val | Asp 440 | Trp | Leu | Leu | Asp | Arg 445 | Phe | Arg | Thr |
| Val | Val 450 | Asn | Val | Leu | Gly | Asp 455 | Ala | Phe | Gly | Thr | Gly 460 | Ile | Val | Glu | Lys |
| Leu 465 | Ser | Lys | Lys | Glu | Leu 470 | Glu | Gln | Met | Asp | Val 475 | Ser | Ser | Glu | Val | Asn 480 |
| Ile | Val | Asn | Pro | Phe 485 | Ala | Leu | Glu | Ser | Ala 490 | Thr | Leu | Asp | Asn | Glu 495 | Asp |
| Ser | Asp | Thr | Lys 500 | Lys | Ser | Tyr | Ile | Asn 505 | Gly | Gly | Phe | Ala | Val 510 | Asp | Lys |
| Ser | Asp | Thr 515 | Ile | Ser | Phe | Thr | Gln 520 | Thr | Ser | Gln | Phe | | | | |